United States Patent
Monsul et al.

(10) Patent No.: US 11,457,633 B2
(45) Date of Patent: Oct. 4, 2022

(54) PROTECTIVE BARRIER COMPOSITIONS AND USES THEREOF

(71) Applicant: Quorum Innovations, LLC, Sarasota, FL (US)

(72) Inventors: Nicholas T. Monsul, Sarasota, FL (US); Eva A. Berkes, Sarasota, FL (US); Frederick T. Boehm, Sarasota, FL (US)

(73) Assignee: QUORUM INNOVATIONS, LLC, Sarasota, FL (US)

( * ) Notice: Subject to any disclaimer, the term of this patent is extended or adjusted under 35 U.S.C. 154(b) by 0 days.

(21) Appl. No.: 17/103,392

(22) Filed: Nov. 24, 2020

(65) Prior Publication Data

US 2021/0298309 A1 Sep. 30, 2021

Related U.S. Application Data

(60) Provisional application No. 63/016,336, filed on Apr. 28, 2020, provisional application No. 62/940,598, filed on Nov. 26, 2019.

(51) Int. Cl.
| | |
|---|---|
| *A01N 63/20* | (2020.01) |
| *C09D 5/14* | (2006.01) |
| *A61K 35/747* | (2015.01) |
| *C12R 1/225* | (2006.01) |

(52) U.S. Cl.
CPC ............ *A01N 63/20* (2020.01); *A61K 35/747* (2013.01); *C09D 5/14* (2013.01); *C12R 2001/225* (2021.05)

(58) Field of Classification Search
None
See application file for complete search history.

(56) References Cited

U.S. PATENT DOCUMENTS

| | | | | |
|---|---|---|---|---|
| 9,706,778 | B2 * | 7/2017 | Berkes | A23L 33/135 |
| 10,004,772 | B2 * | 6/2018 | Berkes | A61P 17/02 |
| 10,617,726 | B2 * | 4/2020 | Berkes | A61P 43/00 |
| 2014/0037688 | A1 | 2/2014 | Berkes et al. | |
| 2017/0020139 | A1 * | 1/2017 | Berkes | A61P 1/00 |

FOREIGN PATENT DOCUMENTS

WO 2017015275 A1 1/2017

OTHER PUBLICATIONS

Aoudia et al. 2015 (Biofilms of Lactobacillus plantarum and Lactobacillus fermentum: Effect on stress responses, antagonistic effects on pathogen growth and immunomodulatory properties; Food Microbiology 53: 51-59). (Year: 2015).*
Subhadra et al. 2015 (Draft Whole-Genome Sequence of Lactobacillus fermentum LfQi6, Derived from the Human Microbiome; Genome Announc 3(3):e00423-15. Doi:10.1128/genomeA.00423-15). (Year: 2015).*
Greenspan et al. 1999 (Defining epitopes: It's not as easy as it seems; Nature Biotechnology, 17:936-937). (Year: 1999).*
Aoudia, N., et al., "Biofilms of Lactobacillus plantarum and Lactobacillus fermentum: Effect on Stress Responses, Antagonistic Effects on Pathogen Growth and Immunomodulatory Properties." Food Microbiology, 2016, 53: 51-59.
Salas-Jara, M.J., et al., "Biofilm Forming Lactobacillus: New Challenges for the Development of Probiotics." Microorganisms, 2016, 4(35): 1-14.
"Uncharacterized Protein LACFE_CDS0840 [Limosilactobacillus fermentum]", NCBI GenBank accession No. AOR74302.1,2017; <https://www.ncbi.nlm.nih.giv/protein/AOR74302.1?report=genbank &log$=protalign>, accessed Oct. 2, 2021.

* cited by examiner

*Primary Examiner* — Mary Maille Lyons
(74) *Attorney, Agent, or Firm* — Saliwanchik, Lloyd & Eisenschenk

(57) ABSTRACT

The subject invention provides compositions and methods of enhancing the barrier function of surfaces and/or objects using biochemical-producing microbes and/or byproducts synthesized by the microbes. Preferred embodiments of the invention provide compositions, and the methods of using the same, comprising a *Lactobacillus* sp., and/or bioactive extracts thereof, derived from human microbiota and capable of growing in biofilm phenotype.

11 Claims, 8 Drawing Sheets

Specification includes a Sequence Listing.

PROTECTIVE BARRIER COMPOSITIONS AND USES THEREOF

CROSS-REFERENCE TO RELATED APPLICATIONS

This application claims priority to U.S. Provisional Patent Application Ser. No. 62/940,598, filed Nov. 26, 2019; and Ser. No. 63/016,336, filed Apr. 28, 2020, each of which are incorporated herein by reference in their entireties.

SEQUENCE LISTING

The Sequence Listing for this application is labeled "SeqList-24Nov20_ST25.txt," which was created on Nov. 24, 2020, and is 2 KB. The Sequence Listing is incorporated herein by reference in its entirety.

BACKGROUND OF THE INVENTION

Chemical and biological threats are a danger to both military and civilian personnel worldwide. Chemical threats can include blister agents and nerve agents, often causing long-term consequences or death. Biological threats can include bacteria, viruses, and fungi dispersed as a means to harm people or other living organisms, such as crops. Common examples of current biological threats include anthrax and plague.

Appropriate protective or counteractive means are essential to limit or prevent the effects of harmful chemical and biological threats. Barriers can be enacted to address multitude of chemical and biological threats.

The barriers can prevent entry or direct contact of the threat to the human. Barriers can be used to neutralize, sequester, or otherwise inactivate the threat. The barriers can prevent adhesion or enhance dispersion of the threat. With respect to biological threats, barriers can actively prevent or stop the means of proliferation, including inhibiting biofilm formation or sporulation.

Like many biological threats, *Yersinia pestis*, the causative agent of plague, is reliant on its ability to form a biofilm. Efficient transmission of *Y. pestis* cells is reliant on biofilm formation in the foregut of a flea, facilitating blocked digestion of a blood meal and the ensuing regurgitation of the blood meal back into the human with *Y. pestis* cells.

Attacking, dissolving, or otherwise weakening the bacterial biofilm matrix could each help to treat the biological agent. Controlling pathogenic bacteria, biofilm, and other substances on the skin or in other organs is a major component in restoring or retaining the health of warfighters and civilians alike. Current therapeutics, however, focus mainly on symptom-control rather than modulating the overall microbiome to inhibit the growth and reduce the adhesion and attachment of chemical or biological threats.

New tools are required to combat growing populations of harmful organisms and substances. Preventing contact or adhesion of harmful organisms or substances, neutralizing or sequestering harmful organisms or substances, and enhancing the durability of barriers are each methods that can work collectively or independently to facilitate improvement in abiotic and biotic barrier functions.

SUMMARY OF THE INVENTION

The subject invention provides compositions and methods for creating a barrier, or enhancing a barrier function, of living organisms and/or non-living substances. Preferred embodiments provide a biofilm-producing bacterium and/or a bioactive substance synthesized by the bacterium, preferably when grown in the biofilm phenotype.

In preferred embodiments, compositions of the subject invention comprise a secreted substance from a biofilm. In one embodiment, the secreted substance can be purified from the culture before addition to the composition. The subject invention also provides compositions comprising a cell lysate in, for example, a lyophilized and/or freeze-dried forms.

In some embodiments, the bacterial strain is *Lactobacillus fermentum* Qi6, also referred to herein as Lf Qi6. In one embodiment, the subject invention provides an isolated or a biologically pure culture of Lf Qi6. In another embodiment, the subject invention provides a biologically pure culture of Lf Qi6, grown as a biofilm. Further provided herein are methods of utilizing the biofilm phenotype, as well as extracts of the biofilm phenotype, and lysates thereof.

In certain embodiments, innate barrier functions are enhanced by modifying barriers in the lung, eye, nose, mouth, trachea, esophagus, ear, stomach, intestine, and/or brain.

In one aspect, the subject invention preferably has one or more biological activities selected from inhibiting antimicrobial activity, inhibiting pathogenic biofilm growth, inhibiting pathogenic biofilm adhesion, promoting pathogenic biofilm detachment, promoting commensal biofilm growth, and enhancing skin barrier functions.

In certain embodiments, the subject invention provides a self-decontaminating surface.

In exemplary embodiments, the pathogenic bacterium is methicillin-resistant *Staphylococcus aureus* (MRSA) and the commensal bacterium is *Staphylococcus epidermidis* (*S. epidermidis*).

In certain embodiments, the composition can enhance the durability of an existing barrier or create a new, durable barrier, and/or to become self-decontaminating. In preferred embodiments, the barrier is stable, retaining its ability to reduce chemical and/or microbial contamination for at least 1, 2, 3, 7, 10, 30, or 180 days or more.

In certain embodiments, the composition creates or enhances a barrier of an inanimate object and/or surface. The objects can be large surfaces, such as ship hulls and airplane wings, or microscopic surfaces, such as the tools used to repair nerves. The compositions and methods of the subject invention can prevent fouling of an inanimate object, which in the case of surgical instruments can prevent bacterial infections. Preferably, the composition and methods of the subject invention prevent or limit direct contact by living organisms or non-living substances on the object, sequester living organisms or non-living substances, and/or inactivate living organisms or non-living substances. In this regard, the surface can be self-decontaminating.

In preferred embodiments, the present invention provides biologically-active proteins having barrier function properties. In a specific embodiment, the present invention provides "Qi611S," a protein having an amino acid sequence according to SEQ ID NO. 1. In certain embodiments, the present invention also provides "Qi611S Proteins," which include Qi611S, as well as biologically-active fragments and variants thereof.

BRIEF DESCRIPTION OF THE FIGURES

FIG. 1 illustrates the inhibition of MRSA biofilm adhesion at a CFU/ml of $3\times10^8$ when exposed to 32 mg/ml of Qi601SL, Qi601SP, Qi601SML, Qi601SMP, or the Qi media as a negative control. The culture was washed twice in deionized water.

Figure 1:
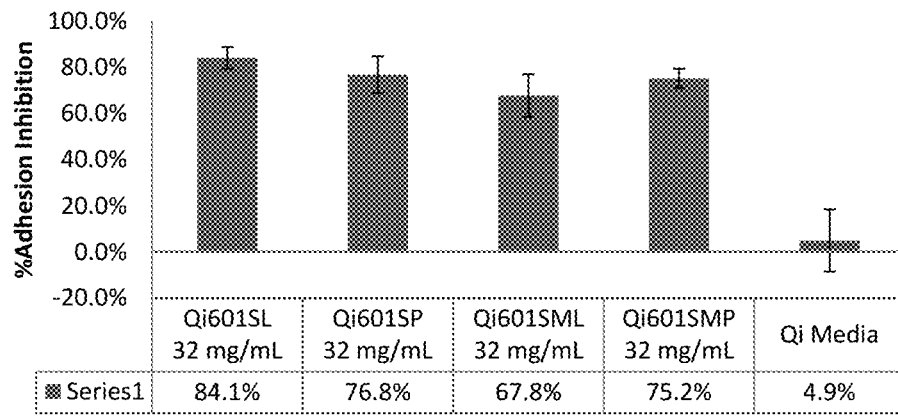
Figure 2:
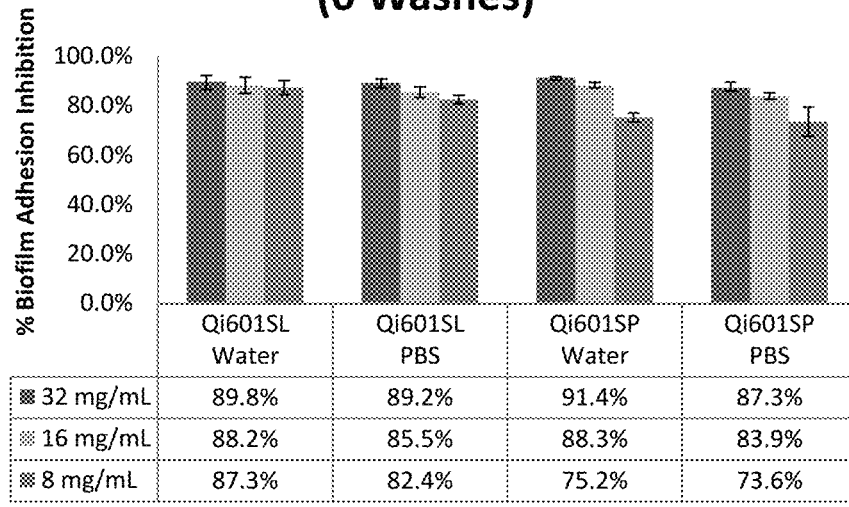
FIG. 2 illustrates the inhibition of MRSA biofilm adhesion at a CFU/ml of $3 \times 10^8$ when exposed to 8 mg/ml, 16 mg/ml, or 32 mg/ml of Qi601SL or Qi601SP in water or PBS. The culture was not washed in deionized water.
Figure 3:
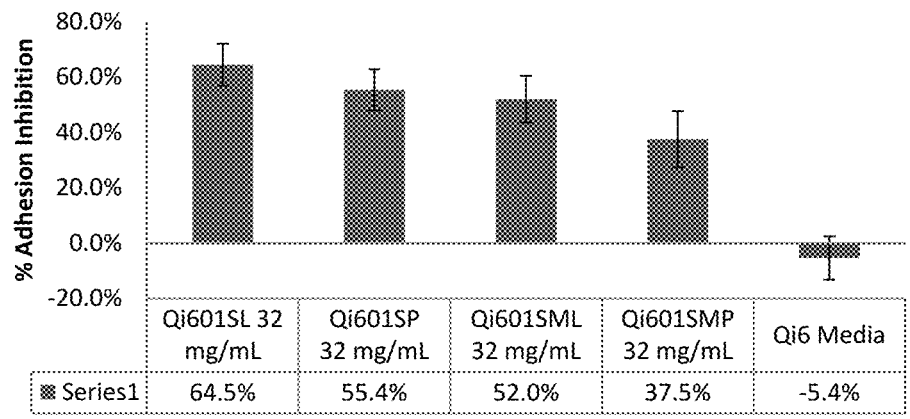
FIG. 3 illustrates the inhibition of MRSA biofilm adhesion at a CFU/ml of $3 \times 10^8$ when exposed to 32 mg/ml of Qi601SL, Qi601SP, Qi601SML, Qi601SMP, or the Qi media as a negative control. The culture was washed thrice in deionized water.
Figure 4:
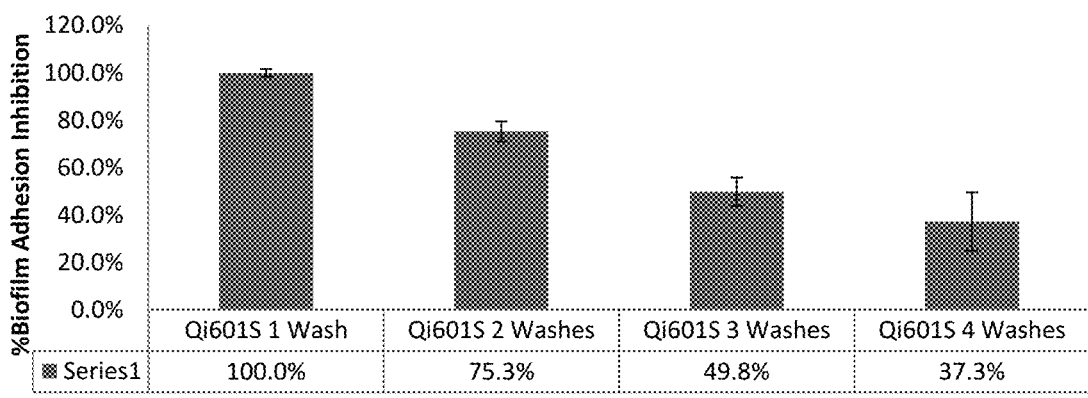
FIG. 4 illustrates the inhibition of MRSA biofilm adhesion at a CFU/ml of $3 \times 10^8$ when exposed to a solution that is 3.2% of Qi601S. The culture was washed once, twice, thrice, or 4-times in deionized water.
Figure 5:
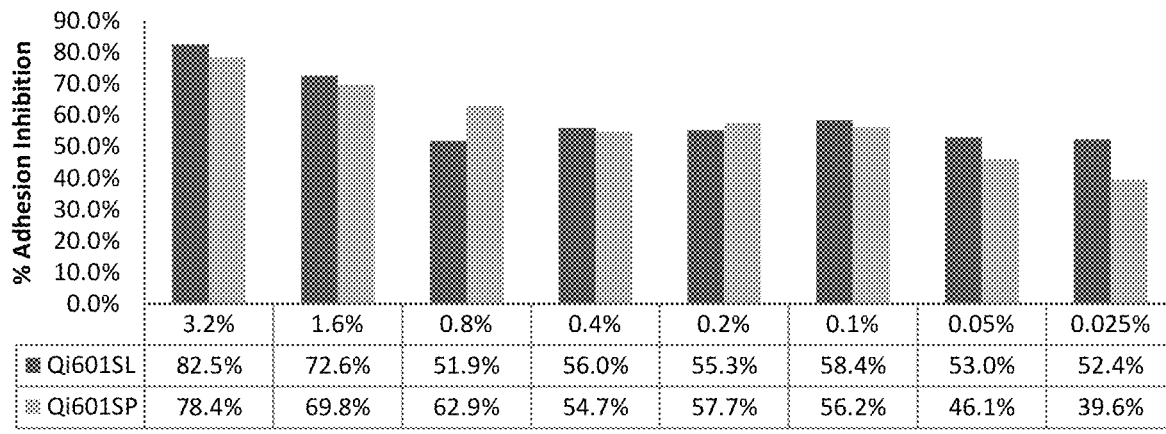

FIG. 5 illustrates the inhibition of MRSA biofilm adhesion at a CFU/ml of $3 \times 10^8$ when exposed to increasing diluted solutions of Qi601SL or Qi601SP, which include 3.2%, 1.6%, 0.8%, 0.4%, 0.2%, 0.1%, 0.05%, and 0.025%. The culture was washed thrice in deionized water.

Figure 6:
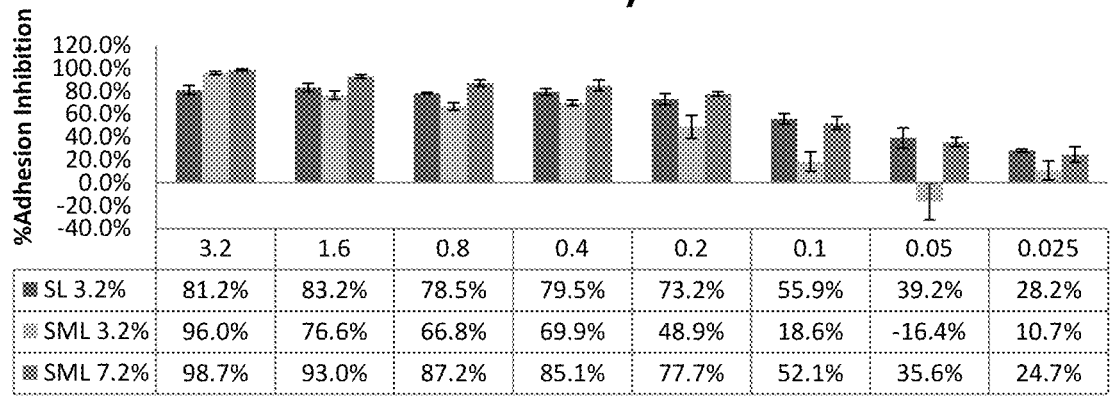

FIG. 6 illustrates the inhibition of MRSA biofilm adhesion at a CFU/ml of $3 \times 10^8$ when exposed to increasing diluted solutions of Qi601SL or Qi601SML, which include 3.2%, 1.6%, 0.8%, 0.4%, 0.2%, 0.1%, 0.05%, and 0.025%. The culture was not washed in deionized water.

Figure 7:
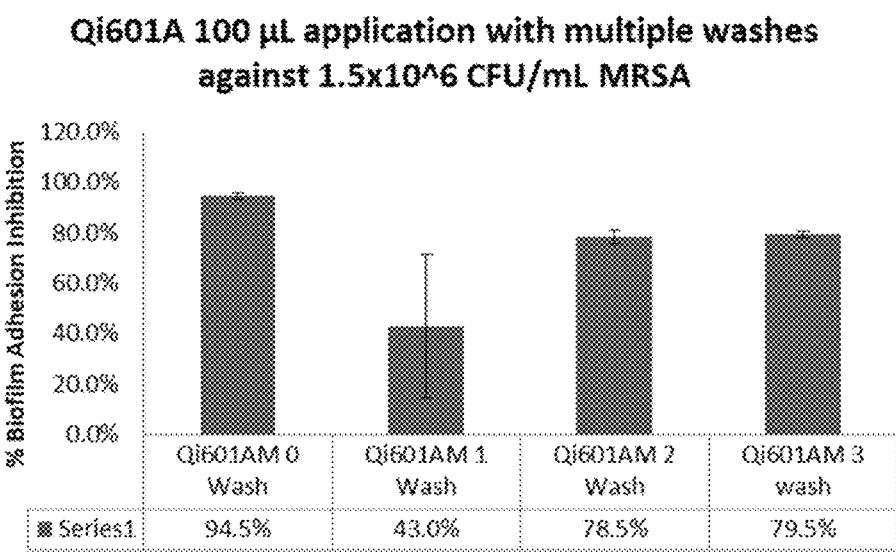

FIG. 7 illustrates the inhibition of MRSA biofilm adhesion at a CFU/ml of $1.5 \times 10^6$ when exposed to Qi601AM. The culture was washed once, twice, thrice, or 0-times in deionized water.

Figure 8:
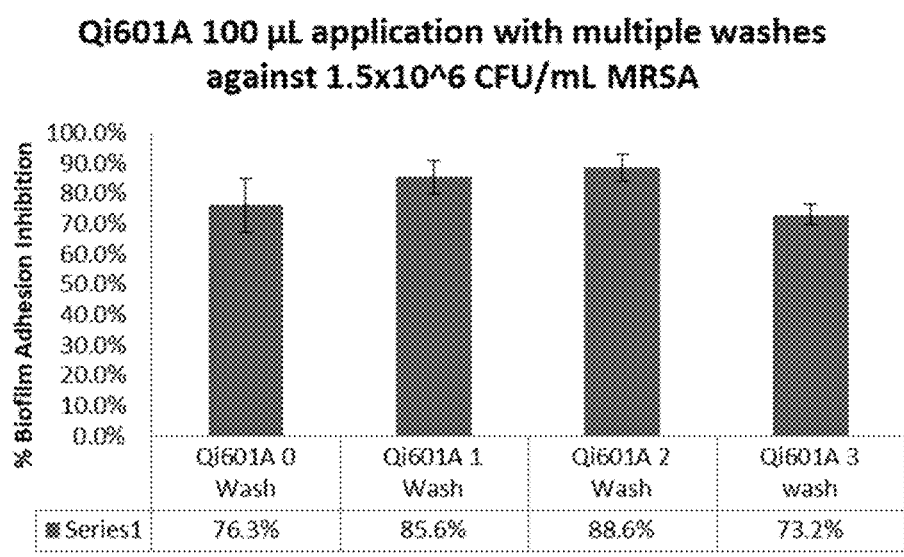

FIG. 8 illustrates the inhibition of MRSA biofilm adhesion at a CFU/ml of $1.5 \times 10^6$ when exposed to Qi601A. The culture was washed once, twice, thrice, or 0-times in deionized water.

Figure 9:
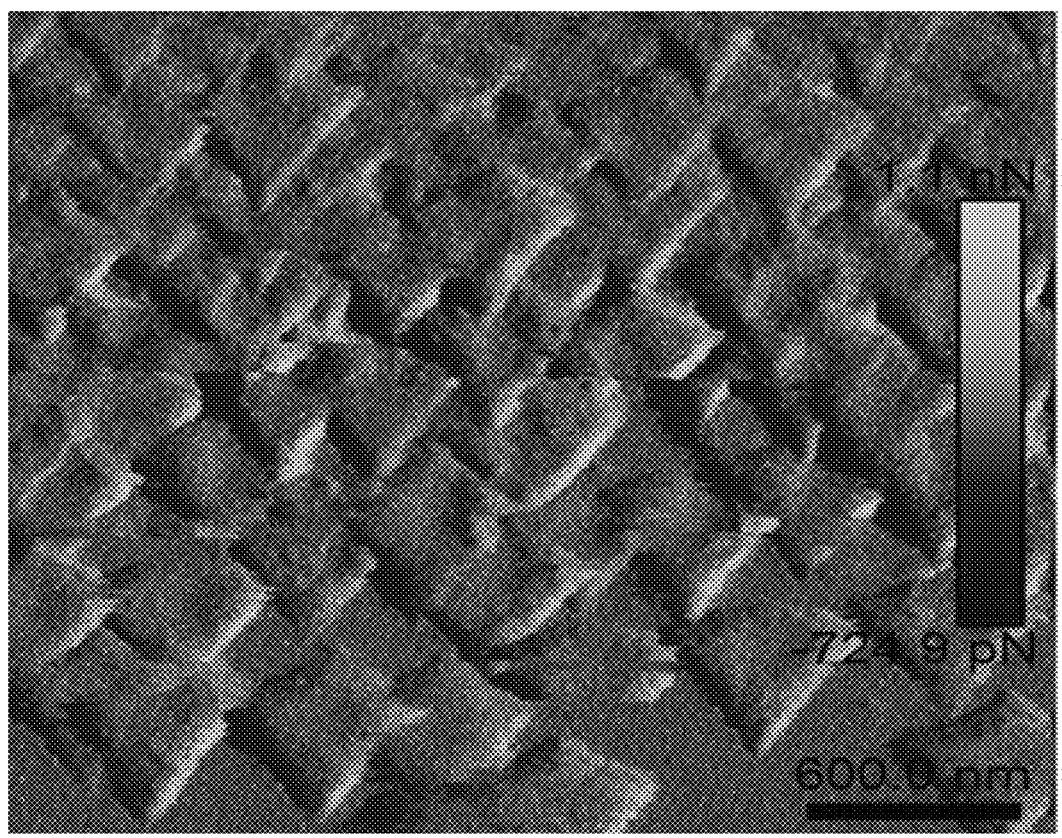

FIG. 9 is an atomic force microscopy image of a composition of the subject invention.

Figure 10:
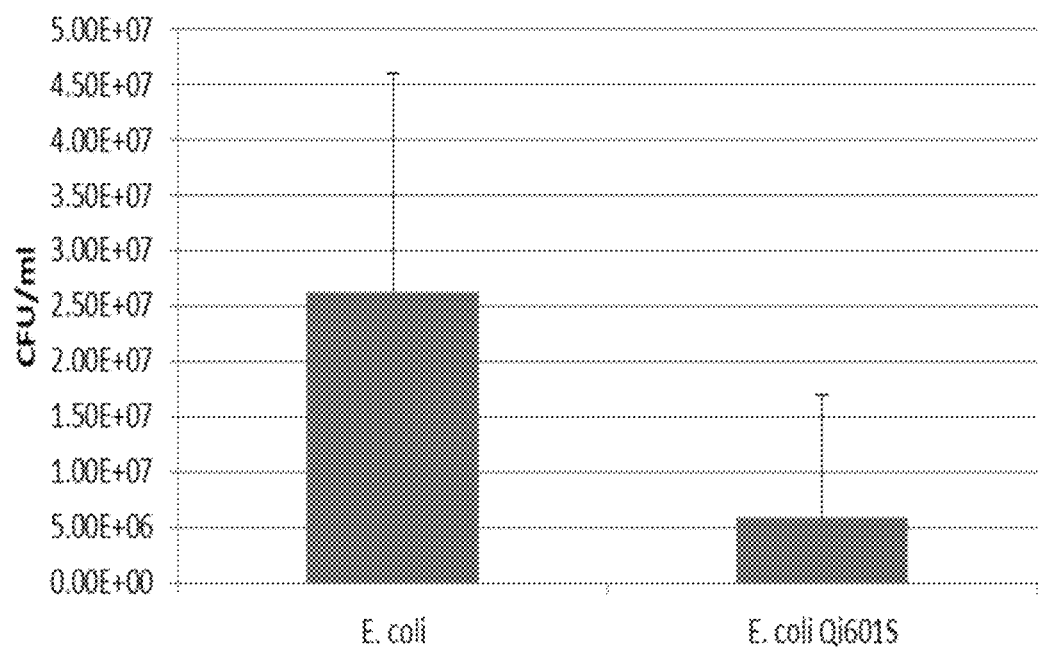

FIG. 10 shows Qi 601S creates an anti-adhesive surface on Caco-2 cells effective against *E. coli*. Cells were split into 24 well plates at $5 \times 10^4$ cells per well and grown for an additional 10 days for differentiation and confluency. Selected wells received overnight pre-treatment with Qi 601S 0.1% v/v followed by PBS wash. *E. coli* K12 was expanded overnight in TSB, $1 \times 10^8$ CFU added to each well and incubated for 3 h. Unbound bacteria were removed by PBS wash. Intestinal cells were lysed with 1% Triton X-100. Bound bacteria were quantified by serial dilution and standard plate counts on TSA and compared against untreated control.

Figure 11:
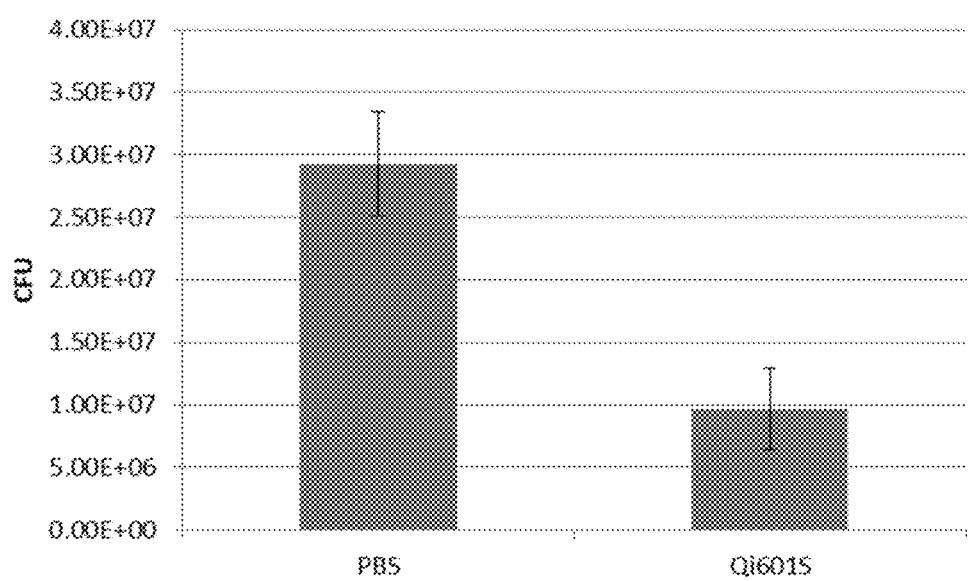

FIG. 11 represents the anti-adhesive surface against MRSA produced by Qi 601S. Qi 601S at 1% v/v in PBS was applied to living human skin in culture for 24 hours and then rinsed. Skin was then incubated with MRSA for 2 days, skin rinsed and then cultured for MRSA colonies. Pre-treatment with Qi 601S demonstrated an over 60% significant reduction in MRSA load compared with untreated skin.

Figure 12:
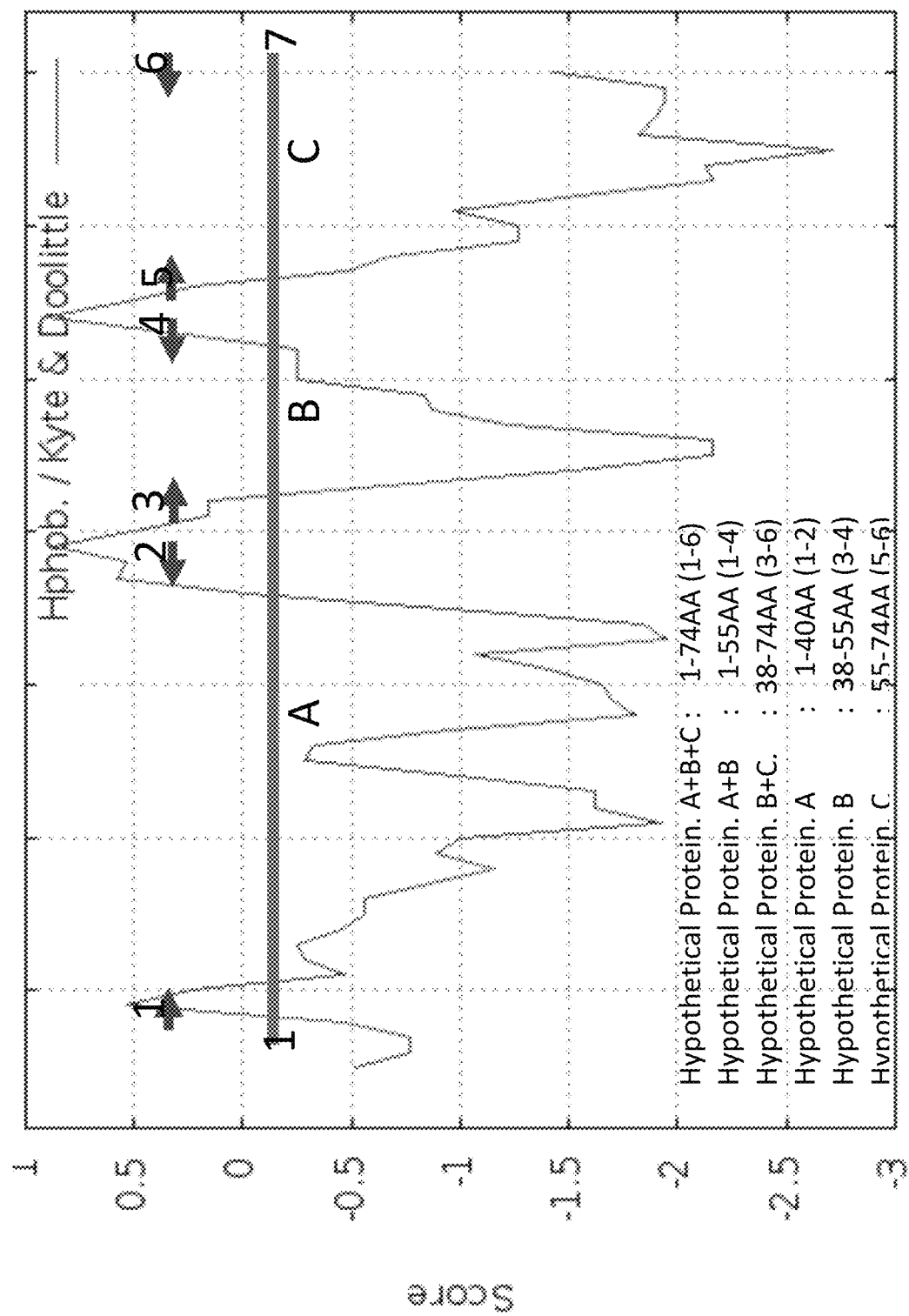

FIG. 12 is a hydrophilicity plot of Qi611S.

Figure 13:
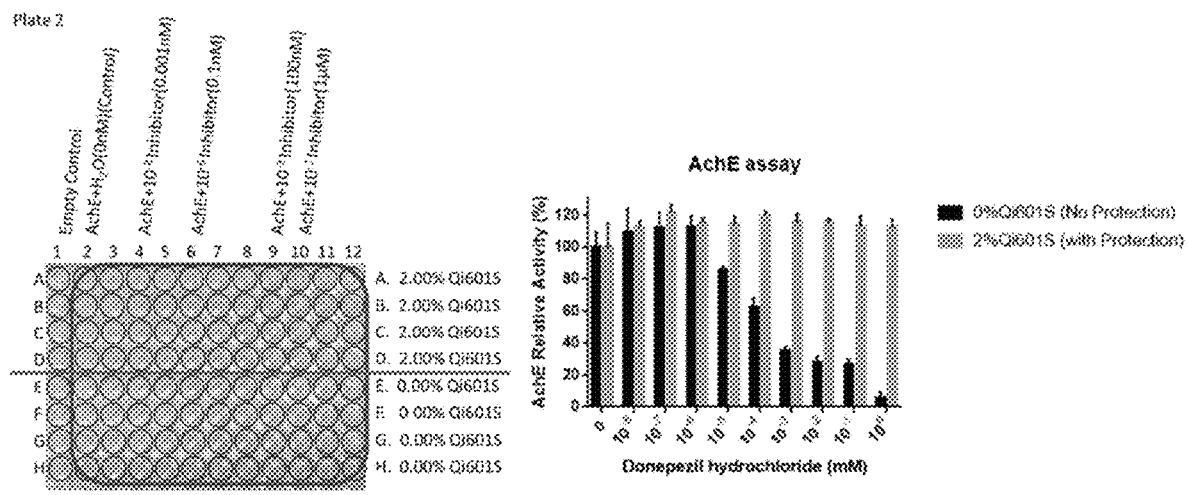

FIG. 13 shows AChE protection by hydrophilic heat stable QI fraction Qi 601S. Qi601S administered at 2% resulted in 100% protection of AChE activity at all doses of donepezil used.

BRIEF DESCRIPTION OF THE SEQUENCES

SEQ ID NO: 1 is the amino acid sequence of the protein designated as "Qi611S."

SEQ ID NO: 2 is Qi611s, a nucleotide sequence encoding the amino acid sequence of SEQ ID NO: 1.

DETAILED DESCRIPTION OF THE INVENTION

The subject invention provides compositions and methods for creating or enhancing a barrier on living organisms or non-living substances. Preferred embodiments of the invention provide compositions, and methods of using the same, comprising a *Lactobacillus* spp., capable of growing in a biofilm phenotype, and/or one or more bioactive extracts thereof. The subject invention also provides compositions of *Lactobacillus* spp., and/or bioactive extracts thereof, in a lyophilized, freeze dried, and/or lysate for.

Advantageously, preferred compositions and treatment methods provided herein are effective in enhancing existing barriers or creating new barriers on both living organisms and non-living substances. Organisms and substances treated with this approach can have decreased fouling, particularly decreased fouling caused by bacterial biofilms.

In certain embodiments, the subject invention provides a self-decontaminating surface. For example, the composition can be self-decontaminating by, in preferred embodiments, preventing, or reducing, microbial, viral and/or chemical adhesion to a surface, including, for example, the cells of an animal tissue. In preferred embodiments, this barrier function is antigen and pathogen agnostic.

In some embodiments, the *Lactobacillus* sp. is *Lactobacillus fermentum* Qi6, referred to herein as Lf Qi6. In one embodiment, the methods utilize the biofilm phenotype, as well as extracts of the biofilm phenotype, including lysates thereof. In preferred embodiments, the compositions comprise bioactive extracts of the Lf Qi6 biofilm.

In preferred embodiments, the present invention provides biologically-active proteins having barrier function properties. In a specific embodiment, the present invention provides "Qi611S," a protein having an amino acid sequence according to SEQ ID NO: 1. In certain embodiments, the present invention also provides "Qi611S Proteins," which include Qi611S, as well as active fragments and variants thereof.

In some embodiments, Qi611S Proteins can be produced by a cell, preferably a bacterial cell. Thus, in specific embodiments, the present invention provides methods for producing a Qi611S Protein, the methods comprising cultivating a cell having a nucleotide sequence that encodes all or a portion of SEQ ID NO: 1, or a variant or fragment thereof, under conditions favorable for expression of the protein. In preferred embodiments, the nucleotide sequence is Qi611s (SEQ ID NO: 2). Optionally, the protein can be purified from the culture.

In one embodiment, the methods utilize a microorganism, e.g., *Lactobacillus fermentum* Qi6, having the Qi611s nucleotide sequence (SEQ ID NO: 2). Qi611s encodes the amino acid sequence according to SEQ ID NO: 1 (Qi611S).

In another embodiment, the cell is a microorganism that has been recombinantly altered to possess the ability to express a Qi611S Protein. In a specific embodiment, the microbe possesses all, or a portion, of the Qi611s gene. Thus, in certain embodiments, the present invention provides a recombinant cell possessing all or a portion of the DNA sequence according to SEQ ID NO: 2, and/or that is capable of expressing a protein having an amino acid sequence according to SEQ ID NO: 1, or a fragment or variant of SEQ ID NO: 1. In an exemplary embodiment, the recombinant cell is *E. coli* BL21 or *E. coli* C43.

Such transformation of cells can be accomplished using techniques well known to those skilled in the microbiological arts. In one embodiment, the nucleotide sequence can be modified to optimize expression of a Qi611S Protein.

In preferred embodiments, the present invention provides compositions comprising a Qi611S Protein and/or a cell comprising all or a portion of a DNA sequence according to SEQ ID NO. 2, and, optionally, a carrier. A culture of the *L. fermentum* microbe has been deposited with the American Type Culture Collection (ATCC), 10801 University Blvd., Manassas, Va. 20110-2209 USA. The deposit has been assigned accession number ATCC No. PTA-122195 by the repository and was deposited on Jun. 10, 2015.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Selected Definitions

"Qi611S" refers to a protein having the amino acid sequence of SEQ ID NO: 1. Reference to a "Qi611S Protein," in the singular or plural, refers to Qi611S, as well as active fragments and variants of 611S.

As used herein, "gene" refers to a segment of DNA, or a nucleotide sequence, capable of expressing a polypeptide and/or amino acid chain. In certain embodiments, the gene includes regions, such as promoter regions, preceding and/or following a coding region.

As used here in, a "biologically pure culture" is one that has been isolated from other biologically active materials, including any materials with which it may have been associated in nature. In a preferred embodiment, the culture has been isolated from all other living cells. In further preferred embodiments, the biologically pure culture has advantageous characteristics compared to a culture of the same microbial species that may exist in nature. The advantageous characteristics can be, for example, enhanced production of one or more desirable growth by-products.

In certain embodiments, purified compounds are at least 60% by weight the compound of interest. Preferably, the preparation is at least 75%, more preferably at least 90%, and most preferably at least 99%, by weight the compound of interest. For example, a purified compound is preferably one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, the term "subject" refers to an animal, needing or desiring delivery of the benefits provided by an active agent (e.g., a pharmaceutical compound). The animal may be, for example, a human, pig, horse, goat, cat, mouse, rat, dog, ape, fish, chimpanzee, orangutan, guinea pig, hamster, cow, sheep, bird (including chicken), as well as any other vertebrate or invertebrate. These benefits can include, but are not limited to, the treatment of a health condition, disease, or disorder; prevention of a health condition, disease, or disorder; promotion of immune health; and/or enhancement of the function of an organ, tissue, or system in the body. The preferred subject, in the context of this invention, is a human. In some embodiments, the subject is suffering from a health condition, disease, or disorder; while, in some embodiments, the subject is in a state of good health (e.g., free from injury or illness) but desires enhanced health and/or functioning of a particular organ, tissue, or body system. The subject can be of any age or stage of development, including infant, toddler, adolescent, teenager, adult, or senior.

As used herein, the terms "therapeutically-effective amount," "therapeutically-effective dose," "effective amount," and "effective dose" are used to refer to an amount or dose of a compound or composition that, when administered to a subject, is capable of treating or improving a condition, disease, or disorder in a subject or that is capable of providing enhancement in health or function to an organ, tissue, or body system. In other words, when administered to a subject, the amount is "therapeutically effective." The actual amount will vary depending on a number of factors including, but not limited to, the particular condition, disease, or disorder being treated or improved; the severity of the condition; the particular organ, tissue, or body system of which enhancement in health or function is desired; the weight, height, age, and health status of the patient; and the route of administration. Prescription of treatment, e.g., decisions on dosage etc., is within the responsibility of general practitioners and other medical doctors, and typically takes into account the disorder to be treated, the condition of the individual patient, the site of delivery, the method of administration and other factors known to practitioners.

As used herein, the term "treatment" refers to eradicating, reducing, ameliorating, or reversing a sign or symptom of a health condition, disease, or disorder to any extent and includes, but does not require, a complete cure of the condition, disease, or disorder. Treating can be curing, improving, or partially ameliorating a disorder. "Treatment" can also include improving or enhancing a condition or characteristic, for example, bringing the function of a particular system in the body to a heightened state of health or homeostasis.

As used herein, "preventing" a health condition, disease, or disorder refers to avoiding, delaying, forestalling, or minimizing the onset of a particular sign or symptom of the condition, disease, or disorder. Prevention can, but is not required to, be absolute or complete; meaning, the sign or symptom may still develop at a later time. Prevention can include reducing the severity of the onset of such a condition, disease, or disorder and/or inhibiting the progression of the condition, disease, or disorder to a more severe condition, disease, or disorder.

As used herein, reference to a "microbe-based composition" or "microbial-sourced composition" means a composition that comprises components that were produced as the result of the growth of microorganisms or other cell cultures. A microbe-based composition may comprise the microbes themselves; or, the microbes may be separated from the broth or media in which they were cultivated, so the composition comprises residual cellular components and/or by-products of microbial growth. The by-products of microbial growth may be, for example, metabolites, cell membrane components, synthesized proteins, and/or other cellular components.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, and/or appropriate carriers (e.g., water or salt solutions). The microbe-based product may comprise mixtures of microbe-based compositions. The microbe-based product may also comprise one or more components of a microbe-based composition that have been processed in some way, such as but not limited to, filtering, centrifugation, lysing, drying, and purification.

As used herein, "harvested" refers to removing some or all of the microbe-based composition from a growth vessel.

As used herein, "applying" a composition or product refers to contacting it with a target or site such that the composition or product can have an effect on that target or site. The effect can be due to, for example, microbial growth and/or the action of a growth byproduct. For example, the microbe-based compositions or products can be sprayed onto objects and/or surfaces.

As used herein, an "isolated" or "purified" protein is substantially free of other compounds, such as cellular material, with which it is associated in nature or in the growth vessel. In certain embodiments, purified compounds are at least 60% by weight (dry weight) of the compound of interest. Preferably, the preparation is at least 75%, more preferably at least 90%, and most preferably at least 99% by weight of the compound of interest. For example, a purified compound is one that is at least 90%, 91%, 92%, 93%, 94%, 95%, 96%, 97%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (i.e., a growth byproduct) or a substance necessary for taking part in a particular metabolic process. A metabolite can be an organic compound that is a starting material (e.g., glucose), an intermediate (e.g., acetyl-CoA), or an end product (e.g., n-butanol) of metabolism. Examples of metabolites include, but are not limited to, biosurfactants, enzymes, acids, solvents, gases, alcohols, proteins, vitamins, minerals, microelements, amino acids, and polymers.

The term "modulate" refers to an alteration (increase or decrease). Such alterations are detected by standard methods known in the art, such as those described herein.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, or 20 as well as all intervening decimal values between the aforementioned integers, such as 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction or 50 to 40, 50 to 30, 50 to 20, and 50 to 10 in the other direction.

By "reduces" is meant as a negative alteration of at least 1%, 5%, 10%, 25%, 50%, 75%, or 100%.

By "increases" is meant as a positive alteration of at least 1%, 5%, 10%, 25%, 50%, 75%, or 100%.

By "reference" is meant a standard or control condition.

As used herein, a "pharmaceutical," "health-promoting compound," or "health-promoting substance" refers to a compound manufactured for use as a medicinal and/or therapeutic drug. As used herein, "contaminant" refers to any substance that causes another substance or object to become fouled or impure. Contaminants can be living or non-living and can be inorganic or organic substances or deposits. In one embodiment, the contaminant is a virus. Living organisms can include bacteria such as cyanobacteria, *Pseudomonas* spp., *Bacillus* spp., *Listeria* spp., *Staphylococcus* spp. *Lactobacillus* spp., and *Lactococcus* spp, eukaryotic organisms such as algae, yeast, fungi, barnacles, and mussels. Furthermore, contaminants can include, but are not limited to, scales, hydrocarbons, such as petroleum, tar sands or asphaltenes; fats, oils and greases (FOG), such as cooking grease and lard; lipids; waxes, such as paraffin; resins; biofilms; or any other substances referred to as, for example, dirt, dust, sludge, crud, slag, grime, scum, plaque, buildup, or residue. Reference to "scale" means any type of scale that results from the precipitation of, for example, barium sulfate, calcium carbonate, calcium sulfate, calcium oxalate, magnesium hydroxide, magnesium oxide, silicates, strontium sulfate, aluminum oxide hydroxides, aluminosilicates, magnetite or nickel ferrite, sodium chloride, silicon dioxide, iron sulfide, iron oxides, iron carbonate, copper, phosphates, oxides, and any other mineral compound that can precipitate and form deposits.

A harmful accumulation of material, including living organism or non-living substances results in the process of "fouling." "Fouling" can result in clogging, scaling, or other undesired buildup. "Fouling" can affect the efficiency, reliability, or functionality of the object.

The transitional term "comprising," which is synonymous with "including," or "containing," is inclusive or open-ended and does not exclude additional elements or method steps not recited. By contrast, the transitional phrase "consisting of" excludes any element, step, or ingredient not specified in the claim. The transitional phrase, "consisting essentially of," limits the scope of a claim to the specified materials or steps "and those that do not materially affect the basic and novel characteristic(s)" of the claimed invention, e.g., the ability to preclude bacterial growth. Use of the term "comprising" contemplates embodiments "consisting" and "consisting essentially" of the recited component(s).

Unless specifically stated or is obvious from context, as used herein, the term "or" is understood to be inclusive. Unless specifically stated or is obvious from context, as used herein, the terms "a," "an," and "the" are understood to be singular or plural.

Unless specifically stated or is obvious from context, as used herein, the term "about" is understood as within a range of normal tolerance in the art, for example, within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value.

As used herein, a "biofilm" is a complex aggregate of microorganisms, such as bacteria, wherein the cells adhere to each other using a matrix usually composed of, but not limited to, polysaccharide material. The cells in biofilms are physiologically distinct from planktonic cells of the same organism, which are single cells that can float or swim in liquid or gaseous mediums, or reside on or in solid or semi-solid surfaces. Individual microbial cells can also be filamentous, banding together in chains of cells, without forming distinct biofilms. Although, the filamentous attributes of the cells can facilitate the creation of biofilms.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. Any compositions or methods provided herein can be combined with one or more of any of the other compositions and methods provided herein.

Other features and advantages of the invention will be apparent from the following description of the preferred embodiments thereof and from the claims. All references cited herein are hereby incorporated by reference.

*Lactobacillus* spp. and the Qi601S Lysate

*Lactobacillus* spp. are Gram-positive rods. *Lactobacillus fermentum* Qi6 (Lf Qi6) can be grown in MRS media at 37° C. The Lf Qi6 culture can be used in the presently presented disclosure or bioactive lysates can be isolated from the Lf Qi6 culture and used in the antibacterial and other barrier enhancing/creating methods and compositions of the subject invention.

Additionally, Lf Qi6 can be grown in a biofilm phenotype. The Lf Qi6 culture can be used according to the present disclosure or bioactive lysates including Qi601S, Qi601SM, Qi601SP, Qi601SL, Qi601SMP, Qi601SML, Qi601ML, Qi601MP, Qi601AM, and Qi601A can be isolated from the Lf Qi6 biofilm culture and used in the antibacterial or other barrier enhancing/creating methods and compositions. Qi601 represents a bioactive lysate of Lf Qi6, with each of the letters accompanying Qi601 representing different fractions isolated from the culture or methods of growth and/or processing of the culture. Qi601S, Qi601SM, Qi601A, and Qi601AM are different fractions isolated from Lf Qi6. "L" and "P" denote a liquid and powder/lyophilized preparation, respectively, of the fractions.

In one method to grow the culture to form a biofilm, the culture can be incubated in 5 ml of MRS broth for 24 hour at 37° C. 1 ml of the culture can then transferred into a T-150 tissue culture plate with 25 ml of MRS broth. 25 ml of MRS media can then be changed every 48 hours to allow the biofilm of Lf Qi6 to grow as a lawn on the bottom of the culture plate. The culture can then be grown for, for example, 7 days to produce a thick biofilm layer. The grown biofilm layer can be subsequently scraped out and suspended in fresh medium. Freezer stacks can be made with glycerol and stored in −80° C.

A biofilm phenotype of Lf Qi6 in frozen stock can be cultured in 10 ml of fresh MRS media for 24 hour at 37° C. 10 ml of culture can be inoculated into 25 L of MRS media with 500 g of sterile glass wool. The biofilm can then be cultured for 72 hours under static conditions at 37° C. The culture can be mixed every 24 hours with a gentle shaking, after which the media and glass wool can be harvested. The biofilm cells can be subsequently detached from the glass wool via sonication. The cells can be further centrifuged to concentrate the biofilm of Lf Qi6, which was then suspended in sterile water. This scale-up yields a biofilm culture at a concentration of 2 g/L.

Qi611S Proteins and Polynucleotide Sequences Encoding 611S Proteins

In preferred embodiments, the present invention provides a protein, as well as fragments and variants thereof, useful for creating a barrier. The present invention further provides nucleotide sequences that encode the protein, as well as fragments and variants thereof.

In certain specific embodiments, a protein of the present invention, referred to as "Qi611S," has a molecular weight of about 8.0 kDA. "Qi611S proteins", which include Qi611S and fragments and variants thereof, can be characterized according to several parameters, including, for example, the ability to create or contribute to a barrier that protects a surface from contamination by, for example, microbes, viruses and/or chemicals.

A Qi611S Protein can further be defined by its amino acid sequence. In a specific embodiment (Qi611S), the protein has the 74 amino acid sequence shown as SEQ ID NO: 1.

In certain embodiments, the proteins provided herein can also be identified based on immunoreactivity with certain antibodies.

In certain embodiments, Qi611S Proteins are produced by the *Lactobacillus fermentum* Qi6 bacterial strain when laboratory growth conditions are used to force the growth into a biofilm phenotype. In preferred embodiment, this bacterial strain possesses the Qi611S DNA sequence (SEQ ID NO: 2), which is capable, under biofilm phenotype conditions, of expressing a protein having SEQ ID NO: 1.

*Lactobacillus fermentum* is a Gram-positive rod. *Lactobacillus fermentum* Qi6 (Lf Qi6) can be grown in MRS media at 37° C.

In certain embodiments, the polynucleotide sequence is Qi611S, which is 222 base pairs and encodes Qi611S; however, in certain embodiments, different DNA sequences can encode the amino acid sequences disclosed herein because of, for example, the redundancy of the genetic code. It is well within the skill of a skilled artisan to create these alternative DNA sequences encoding the Qi611S Proteins.

As used herein, "variants" of a protein refer to sequences that have one or more amino acid substitutions, deletions, additions, or insertions. In preferred embodiments, these substitutions, deletions, additions or insertions do not materially adversely affect the barrier activity of Qi611S. Variants that retain barrier activity are within the scope of the present invention.

"Fragments" of Qi611S and its variants are also within the scope of Qi611S Proteins, so long as the fragment retains one or more biological properties of Qi611S. Preferably the one or more biological activities include barrier promotion activity. Preferably, the fragment is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the full length Qi611S. The fragment may comprise, for example, one or more hydrophilic domains of Qi611S or variant. These domains may be directly connected with intervening amino acids removed. Hydrophilic domains can be readily identified using standard procedures known in the art and as exemplified in FIG. 12.

The subject invention further contemplates fusion constructs where a Qi611S Protein is attached, directly or indirectly (e.g., via a linker), to another moiety that may be, for example, a targeting moiety (e.g., ligand, antibody, or aptamer), a toxin, a carrier, a label, or an activity enhancer.

The subject invention further contemplates antibodies (e.g., polyclonal, monoclonal, chimeric, and humanized) to the Qi611S Proteins. These antibodies can be readily prepared by a person of ordinary skill in the art having possession of the teachings provided herein. These antibodies can be used for, for example, protein purification.

In certain embodiments, a polynucleotide encoding a Qi611S Protein can be isolated, amplified and ligated into a vector. A "vector," "plasmid," or "plasmid vector" is a DNA molecule used to transfer DNA to a cell, often from one cell to another (a host cell). The vector can be replicated in the host cell; or, the vector can be a means to incorporate DNA into (or remove DNA from) a cell. A variety of means can be used to introduce a vector into a host cell. Some cells can uptake a vector without any action by one skilled in the art other than placing the vector in the cell culture. Others require chemical modification. Regardless of the means with which a cell can uptake a vector, once a host cell has the ability to do so, it is now a "competent" cell.

In certain embodiments, the present invention pertains to the genetic transformation of host cells so as to provide these cells with the ability to produce a Qi611S protein. For example, a vector with Qi611S (or other polynucleotide encoding a Qi611S Protein) can be transformed into a host cell (e.g., a microorganism, a plant, a fungal, and/or an animal cell) allowing for the use of recombinant cells for the production of the Qi611S Protein.

In preferred embodiments, the host cell is a strain of *Escherichia coli*, e.g., *E. coli* BL21 or *E. coli* C43. Alternatively, the ability to transform cells, other than *E. coli*, into competent cells is well understood in the art, this includes cells chosen based on, e.g., their transformation ability, ability and efficiency for heterologous protein expression, stability of the protein in the host, presence of auxiliary genetic capabilities, lack of mammalian toxicity, ease of killing and fixing without damage to the protein, ease of cultivation and/or formulation, ease of handling, economics, storage stability and the like.

It will be recognized by those skilled in the art that DNA sequences of the subject invention may vary due to the degeneracy of the genetic code and codon usage. All DNA sequences that encode a Qi611S Protein are contemplated. Thus, all polynucleotide sequences that encode a Qi611S Protein are included in this invention, including DNA (optionally including an ATG preceding the coding region) that encodes SEQ ID NO: 1. The subject invention also includes polynucleotides having codons that are optimized for expression in a host cell, including any of the specific types of cells referred to herein. Various techniques for creating optimized sequences are known in the art.

Additionally, it will be recognized by those skilled in the art that allelic variations may occur in the DNA sequences that will not significantly change activity of the amino acid sequences of the peptides that the DNA sequences encode. All such variant DNA sequences are included within the scope of this invention.

The skilled artisan will understand that the exemplified sequences can be used to identify, produce, and use additional nucleotide sequences that encode Qi611S Proteins. Variant DNA sequences having at least 90%, or at least 95% identity to a recited DNA sequence and encoding a Qi611S Protein are included in the subject invention. Other numeric ranges for variant polynucleotides and amino acid sequences are provided below (e.g., 50-99%). Following the teachings herein and using knowledge and techniques well known in the art, the skilled worker will be able to make a large number of operative embodiments having variant DNA sequences without the use of undue experimentation. Specifically contemplated are homologs from other strains or species.

The fragments and the mutational, insertional, and deletional variants of the polynucleotide and amino acid sequences of the invention can be used in the same manner as the exemplified sequences so long as the fragments and variants have substantial sequence similarity with the original sequence. As used herein, substantial sequence similarity refers to the extent of nucleotide or amino acid sequence similarity that is sufficient to enable the variant or fragment sequence to function in the capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage. The identity and/or similarity can also be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid identity/similarity and/or homology will typically be highest in critical regions of the protein that account for biological activity and/or are involved in the determination of three-dimensional configuration that ultimately is responsible for the biological activity. In this regard, certain amino acid substitutions are acceptable and can be expected if these substitutions are in regions that are not critical to activity or are conservative amino acid substitutions that do not affect the three-dimensional configuration of the molecule. For example, amino acids may be placed in the following classes: non-polar, uncharged polar, basic, and acidic. Conservative substitutions, whereby an amino acid of one class is replaced with another amino acid of the same type, fall within the scope of the subject invention so long as the substitution does not materially alter the biological activity of the compound. The following (Table 1) is a list of examples of amino acids belonging to each class.

TABLE 1

Classification of amino acids based on physical properties.

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the protein.

Formulation and Delivery of the Lf Qi6 and the Qi601S Lysate

The subject invention provides compositions and methods for enhancing barrier functions. Preferred embodiments of the invention provide compositions, and methods of using the same, comprising a novel lysate. The subject invention also provides compositions in lyophilized and/or freeze dried forms.

Advantageously, preferred compositions and treatment methods provided herein are effective in treating or preventing bacterial and/or viral infection, preventing fouling, limiting or eliminating contact between an object and a noxious substance or organism, inactivating a harmful organism or substance, and/or increasing the durability of a barrier.

In certain embodiments, the subject invention provides a self-decontaminating surface.

In one aspect, the subject invention provides compositions for preventing or reducing chemical or microbial contamination of a surface and/or for treating bacterial and/or viral infections, comprising a biologically pure bacterial strain, and/or a bioactive extract thereof, and one or more pharmaceutically-acceptable excipients. Additionally, the composition can be composed of the bacterial strain capable of growing in both planktonic and biofilm phenotypes, the composition having one or more biological activities selected from, general antimicrobial activity, inhibiting pathogenic biofilm growth, inhibiting pathogenic biofilm adhesion, promoting pathogenic biofilm detachment, promoting commensal biofilm growth, and enhancing skin barrier functions.

In some embodiments, a self-decontaminating surface prevents microbial or viral adhesion and, in specific embodiments, subsequent biofilm formation and/or detach existing biofilms, while reinforcing the barrier function of the involved substrate. In specific embodiments, the compositions comprise one or more heat-stable biofilm proteins that block the formation of hazardous biofilms and/or other contaminants when applied to a surface such as skin, and biologic surfaces such as polystyrene and glass. These compositions improve skin immunity, physical cohesion and overall barrier function of the skin. These compositions provide an alternative to traditional chemical surface decontamination and pharmacologic antimicrobials. Because of their lack of toxicity on human biological surfaces, biomedical applications are broad, and include use as a self-decontaminating material applied topically to the skin, intestine, stomach, lung, eye, mouth, sinuses, nose, ear, trachea or esophagus of a subject.

As used herein the term "extract" refers to a composition obtained by processing a bacterial culture. The processing may involve, for example, physical and/or chemical treatment. The physical and/or chemical treatment may comprise, for example, filtering, centrifugation, sonication, pressure treatment, radiation treatment, lysing, treatment with solvents or other chemicals, and combinations of these treatments. The extract can be in the form of, for example, a supernatant such as that produced via centrifugation. The extract can also include cell mass obtained through centrifugation. The cells may be intact or not intact, viable or not viable. The extract may comprise cell membrane components and/or intracellular components. In certain embodiments, the extract is at least 80, 85, 90, or 95%, by weight, cell mass. In certain embodiments, at least 95% of the intact cells are non-viable. In certain embodiments, less than 10% of the cell mass in the extract is intact cells.

Human skin comprises two compartments, the deep compartment (the dermis) and the surface compartment (the epidermis). The skin constitutes a barrier against external attacks, particularly chemical, mechanical, and/or infectious attacks, as well as a number of defensive reactions against environmental factors such as, for example, climate, ultraviolet rays, and tobacco, and/or xenobiotic factors, such as, for example, microorganisms. This property is referred to as the skin barrier function and is mainly provided by the most superficial layer of the epidermis, namely the stratum corneum. Detrimental changes in the barrier can be reflected by, for example, cutaneous discomfort, sensory phenomena and/or cutaneous dryness.

Compositions according to some embodiments of the invention are useful for preventing a reduction in the barrier function and/or to repair or regenerate barrier function. Disorders associated with disruption of the skin and/or mucosal barrier include, but are not limited to, psoriasis, icthyosis, sarcoidosis, atherosclerosis, inflammatory bowel disease, acne (including hidradenitis suppurativa), burns, diaper rash, Netherton's syndrome, actinic keratosis, dermatomycoses, dermatosis or ectodermal dysplasia, atopic dermatitis, contact dermatitis, seborrheic dermatitis, vulgaris, eosinophilic esophagitis, filaggrin deficiency, and other disorders associated with damage or breakdown of the skin and/or mucosal barrier.

In some embodiments, the methods of the subject invention promote repair, regeneration, or other enhancement of the barrier, including repair or regeneration of a mucous membrane. Mucous membranes include mucosa of the mouth (including mucosa of the cheek, the soft palate, the tongue, including the under surface of the tongue and the floor of the mouth), the nose, the throat (including mucosa of the pharynx, the larynx, the trachea and the esophagus), the bronchi, the lungs, the eye, the ear, the gastrointestinal tract, the vagina, the penis, the urethra, the bladder, and the anus. In certain embodiments, the compositions of the subject invention can also be used in the treatment of acute and chronic viral infections. In particular, the subject invention can be used for the treatment of, or barrier to entry of, chronic Epstein-Barr virus, influenza, coronavirus (including COVID-19), cytomegalovirus and other herpes-type virus infection, which are ubiquitous in the population and are associated with a decrease on the immune surveillance. Some viral infections can lead to cancer. For example, Epstein-Barr virus infection can be a risk factor of Hodgkin's lymphoma, a caner of lymphocytes.

Advantageously, preferred composition of the subject invention can be heat sterilized and retain activity. In one embodiment, the composition of the subject invention retains the ability to resist microbial colonization of a surface even after being subjected to 254° F. and 21 pounds per square inch of pressure for 30 minutes. In preferred embodiments, the active is maintained at pH 4.0 to 8.0, 4.5 to 7.5 or 5.0 to 7.5.

The compositions provided herein may also include other pharmaceutically-acceptable ingredients known to those skilled in the art, including, but not limited to, pharmaceutically-acceptable carriers, adjuvants, excipients, diluents, fillers, buffers, preservatives, anti-oxidants, lubricants, stabilizers, solubilizers, surfactants (e.g., wetting agents), masking agents, and coloring agents. The formulations may further comprise other active agents including, for example, other therapeutic or prophylactic agents.

As provided herein, "pharmaceutically-acceptable" refers to approved or approvable by a regulatory agency of the US Federal Government or a state government or listed in the U.S. Pharmacopeia or other generally recognized pharmacopeia for use in animals, including humans.

"Pharmaceutically-acceptable excipient, carrier or adjuvant" refers to an excipient, carrier or adjuvant that can be administered to a subject, together with an active ingredient, and which does not destroy the pharmacological activity thereof and is nontoxic when administered in doses sufficient to deliver a therapeutic amount of the compositions provided herein.

Infections occur where disease causing microorganisms invade the tissues of the body. Those microorganisms and the toxins that they produce react with the tissues of the body, often causing immune reactions by the infected host.

Infections may be caused by bacteria, viruses, viroids, fungi and other parasites. Infections may occur via any of the tissues of the body, such as the skin, gut or membranes. In specific embodiments, the subject invention provides compositions for the treatment and/or prevention of infection of the external surface of the body, and particularly of the skin. The infection may be caused by a bacterium, such as pathogenic *Staphylococcus aureus* bacteria. The pharmaceutical compositions provided herein may be applied separately, sequentially or simultaneously with exposure to the infective agent. In other embodiments, the subject invention provides materials and methods for treating intestinal and other internal disorders.

*S. aureus* is a transient colonizer of skin predominantly in the moist, warm regions of the body such as the groin, axilla and the anterior nares. Up to 60% of the world's populations are intermittent carriers while another 20% may be stably colonized. While normal carriage is asymptomatic, *S. aureus* may invade tissues (e.g., through broken skin) where it causes diseases ranging from the relatively minor impetigo and scalded skin syndrome, to life threatening conditions such as septicemia. Furthermore, *S. aureus* infection is often a secondary phenomenon in skin with underlying conditions such as atopic dermatitis (AD).

Exemplary compositions provided by the subject invention are useful for the treatment of, or barrier to, infections by a number of pathogenic bacteria including, but not limited to, *Staphylococcus* spp. (*Staphylococcus saprophyticus, Staphylococcus xylosus, Staphylococcus lugdunensis, Staphylococcus schleiferi, Staphylococcus caprae, Staphylococcus saprophyticus, Staphylococcus hominis, Staphylococcus aureus*), *Pseudomonas* spp., *Enterococcus faecalis*, vancomycin-resistant *Enterococcus* (VRE), *Bacillus cereus, Bacillus subtilis, Listeria monocytogenes, Streptococcus pyrogenes, Streptococcus salivariu, Streptococcus mutans*, and *Streptococcus pneumonia*. Other pathogenic bacteria will be readily recognized by a person skilled in the art.

In certain embodiments, the subject invention provides antibacterial compositions in the form of cleaning products, washes, surface coatings or other compositions, which are not for medical treatment of the human or animal body. Thus, in specific embodiments, these compositions are used to disinfect, or provide a barrier to microbial colonization of, inanimate surfaces. In certain embodiments, the subject invention provides a self-decontaminating surface.

In another aspect, the subject invention provides a method of treating, or providing a barrier against, human dermatological disorders comprising administering to a subject an effective amount of the composition, the composition preferably comprising one or more bioactive extracts of the Lf Qi6 biofilm.

A composition may be administered alone or in combination with other treatments, either simultaneously or sequentially dependent upon the condition to be treated or protected against. The compositions provided herein may be dissolved in, suspended in, or admixed with one or more other acceptable ingredients. The compositions may also be presented in a liposome or other microparticle.

In preferred embodiments, the compositions are formulated for topical administration, particularly for use or application to, or on, the skin. Such formulations may be useful for removing, killing, or preventing the adhesion, colonization and/or accumulation of undesirable substances such as pathogenic bacteria, such as MRSA, on a biological or non-biotic surface, or inhibiting the action or growth of the bacteria. Furthermore, in specific embodiments, compositions comprising biofilm, or the extracts thereof, of Lf Qi6 have the advantage of promoting the growth of commensal bacteria in the human skin microbiome. Non-limiting examples of the commensal bacteria include, but are not limited to, *Staphylococcus epidermidis, Staphylococcus warneri, Streptococcus mitis, Propionibacterium acnes, Corynebacterium* spp., *Acinetobacter johnsonii*, and *Pseudomonas aeruginosa*.

The compositions provided herein may suitably be provided as a patch, adhesive plaster, bandage, dressing, or the like which is impregnated with, or coated with, the microbial biofilm and/or one or more extracts thereof and, optionally, one or more other acceptable ingredients, including, for example, penetration, permeation, and absorption enhancers.

The compositions according to embodiments of the invention may be useful for treating biomaterials, implants and prosthesis (including stents, valves, eyes, hearing aids, gastric bands, dentures, and artificial joint replacement), surgical instruments or other medical devices prior to administration to, or treatment of, or use with, a subject. The antibacterial compositions may be useful for treating surfaces prone to colonization or exposure to bacteria or viruses, such as handrails, food preparation surfaces, kitchen surfaces or equipment, tables, sinks, toilets or other bathroom hardware.

The compositions may comprise agents in addition to the microbial (e.g., Lf Qi6) biofilm or its bioactive extracts, such as cleaning agents, stabilizers, anionic surfactants, perfumes, chelating agents, acids, alkalis, buffers and/or detergents. Such agents may facilitate or enhance the antibacterial and/or barrier properties of the compositions, such as killing or inhibiting bacteria and/or viruses, or preventing the colonization of a surface.

Formulations suitable for dermal and/or transdermal administration include, but are not limited to, gels, pastes, ointments, creams, lotions, and oils, as well as patches, adhesive plasters, bandages, dressings, depots, cements, glues, and reservoirs.

Ointments are typically prepared from the cosmetic compositions provided herein and a paraffinic or a water-miscible ointment base.

Creams are typically prepared from the cosmetic compositions provided herein and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol, polyethylene glycol, and mixtures thereof.

As would be readily appreciated by one skilled in the art, formulations according to the subject invention could also comprise other alcohols, such as, for example, isopropyl alcohol or ethanol, and could also cover other alcohol based formulations, for example alcohol-based hand sanitizers.

The topical formulations may desirably include a compound that enhances absorption or penetration of the active compound through the skin or other affected areas. Examples of such dermal penetration enhancers include dimethylsulfoxide and related analogs.

Emulsions are typically prepared from the cosmetic compositions provided herein and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both oil and a fat. Together, the emulsifier(s), with or without stabilizer(s), make up the so-called emulsifying wax, and the wax together with the oil and/or fat make up the so-called emulsifying ointment base, which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used. Other formulations include dental sprays, mouthwashes, toothpastes, lozenges, antibacterial washes, drinks (e.g., milk, yoghurt), food items (such as yogurt, ice cream, candy bars), or powdered foods (such as powdered milk).

The compositions provided herein may contain a single (unit) dose of probiotic bacteria, or lysate, or extract thereof. Suitable doses of probiotic bacteria (intact, lysed or extracted) may be in the range 104 to 1012 cfu, e.g., one of 104 to 1010, 104 to 108, 106 to 1012, 106 to 1010, or 106 to 1080 cfu. In some embodiments, doses may be administered once or twice daily. In some embodiments, a composition for use according to the present invention may comprise at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% by weight of the extracts. In some embodiments, the compositions may comprise, one of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, by weight of the Lf Qi6 extracts.

For the purpose of the present invention the abbreviation cfu shall designate a "colony forming unit" that is defined as the number of bacterial cells as revealed by microbiological counts on agar plates.

In one embodiment, the subject composition is formulated as an orally-consumable product, such as a food item, capsule, pill, or drinkable liquid. An orally deliverable health-promoting compound is any physiologically active substance delivered via initial absorption in the gastrointestinal tract or into the mucus membranes of the mouth. The composition can also be formulated as a solution that can be administered via, for example, injection, which includes intravenously, intraperitoneally, intramuscularly, intrathecally, or subcutaneously. In other embodiments, the subject composition is formulated to be administered via the skin through a patch or directly onto the skin for local or systemic effects. The compositions can also be administered sublingually, buccally, rectally, or vaginally. Furthermore, the compositions can be sprayed into the nose for absorption through the nasal membrane, nebulized, inhaled via the mouth or nose, or administered in the eye or ear.

Orally-consumable products, according to the invention, are any preparations or compositions suitable for consumption, for nutrition, for oral hygiene, or for pleasure and are products intended to be introduced into the human or animal oral cavity, to remain there for a certain period of time, and then either to be swallowed (e.g., food ready for consumption or pills) or to be removed from the oral cavity again (e.g., chewing gums or products of oral hygiene or medical mouth washes). While an orally-deliverable pharmaceutical can be formulated into an orally consumable product, and an orally consumable product can comprise an orally deliverable pharmaceutical, the two terms are not meant to be used interchangeably herein.

Orally-consumable products include all substances or products intended to be ingested by humans or animals in a processed, semi-processed, or unprocessed state. This also includes substances that are added to orally consumable products (particularly food and pharmaceutical products) during their production, treatment, or processing and intended to be introduced into the human or animal oral cavity.

Orally-consumable products can also include substances intended to be swallowed by humans or animals and then digested in an unmodified, prepared, or processed state. The orally consumable products, according to the invention, also include casings, coatings, or other encapsulations that are intended to be swallowed together with the product or for which swallowing is to be anticipated.

In one embodiment, the orally-consumable product is a capsule, pill, syrup, emulsion, or liquid suspension containing a desired orally deliverable substance. In one embodiment, the orally consumable product can comprise an orally deliverable substance in powder form, which can be mixed with water or another liquid to produce a drinkable orally consumable product.

In some embodiments, the orally-consumable product, according to the invention, can comprise one or more formulations intended for nutrition or pleasure. These include baking products (e.g., bread, dry biscuits, cake, and other pastries), sweets (e.g., chocolates, chocolate bar products, other bar products, fruit gum, coated tablets, hard caramels, toffees and caramels, and chewing gum), alcoholic or non-alcoholic beverages (e.g., cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, and fruit or vegetable juice preparations), instant beverages (e.g., instant cocoa beverages, instant tea beverages, and instant coffee beverages), meat products (e.g., ham, fresh or raw sausage preparations, and seasoned or marinated fresh meat or salted meat products), eggs or egg products (e.g., dried whole egg, egg white, and egg yolk), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, whey, butter, buttermilk, and partly or wholly hydrolyzed products containing milk proteins), products from soy protein or other soy bean fractions (e.g., soy milk and products prepared thereof, beverages containing isolated or enzymatically treated soy protein, soy flour containing beverages, preparations containing soy lecithin, fermented products, such as tofu or tempeh products prepared thereof and mixtures with fruit preparations and, optionally, flavoring substances), fruit preparations (e.g., jams, fruit ice cream, fruit sauces, and fruit fillings), vegetable preparations (e.g., ketchup, sauces, dried vegetables, deep-freeze vegetables, pre-cooked vegetables, and boiled vegetables), snack articles (e.g., baked or fried potato chips (crisps) or potato dough products and extrudates on the basis of maize or peanuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening or whitening beverages or other food). The present compositions may also serve as semi-finished products for the production of other compositions intended for nutrition or pleasure.

The subject composition can further comprise one or more pharmaceutically acceptable carriers, and/or excipients, and can be formulated into preparations, for example, solid, semi-solid, liquid, or gaseous forms, such as tablets, capsules, powders, granules, ointments, solutions, suppositories, injections, inhalants, and aerosols.

Carriers and/or excipients, according the subject invention, can include any and all solvents, diluents, buffers (such as neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol), and the like. The use of carriers and/or excipients in the field of drugs and supplements is well known. Except for any conventional media or agent that is incompatible with the target health-promoting substance or with the adjuvant composition, carrier or excipient use in the subject compositions may be contemplated.

In one embodiment, the composition can be made into aerosol formulations so that, for example, it can be nebulized or inhaled. Suitable pharmaceutical formulations for administration in the form of aerosols or sprays are, for example, solutions, suspensions, or emulsions. Formulations for oral or nasal aerosol or inhalation administration may also be formulated with illustrative carriers, including, for example, saline, polyethylene glycol or glycols, DPPC, methylcellulose, or in mixture with powdered dispersing agents or fluorocarbons. Aerosol formulations can be placed into pressurized propellants, such as dichlorodifluoromethane, propane, nitrogen, fluorocarbons, and/or other solubilizing or dispersing agents known in the art. Illustratively, delivery may be by use of a single-use delivery device, a mist nebulizer, a breath-activated powder inhaler, an aerosol metered-dose inhaler (MDI), or any other of the numerous nebulizer delivery devices available in the art. Additionally, mist tents or direct administration through endotracheal tubes may also be used.

In one embodiment, the composition can be formulated for administration via injection, for example, as a solution or suspension. The solution or suspension can comprise suitable non-toxic, parenterally-acceptable diluents or solvents, such as mannitol, 1,3-butanediol, water, Ringer's solution, or isotonic sodium chloride solution, or suitable dispersing or wetting and suspending agents, such as sterile, non-irritant, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600, and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance is an acceptable isotonic solution, such as 5% dextrose or 0.9% sodium chloride; or 0.01-0.2% dipalmitoyl diphosphatidylcholine in USP WFI and 1 to 10% squalene or parenteral vegetable oil-in-water emulsions.

In one embodiment, the composition can be formulated for administration via topical application onto the skin, for example, as topical solutions, which include rinse, spray, drop, lotion, gel, ointment, cream, foam, powder, solid, sponge, tape, vapor, paste, tincture, or a transdermal patch. Suitable formulations of topical applications can comprise, in addition to any of the pharmaceutically active carriers, emollients, such as carnauba wax, cetyl alcohol, cetyl ester wax, emulsifying wax, hydrous lanolin, lanolin, lanolin alcohols, microcrystalline wax, paraffin, petrolatum, polyethylene glycol, stearic acid, stearyl alcohol, white beeswax, or yellow beeswax. Additionally, the compositions may contain humectants, such as glycerin, propylene glycol, polyethylene glycol, sorbitol solution, and 1,2,6 hexanetriol or permeation enhancers, such as ethanol, isopropyl alcohol, or oleic acid.

One bacteria-based product of the subject invention is simply the growth media containing the bacteria and/or the microbial metabolites produced by the bacteria and/or any residual nutrients. The product of growth may be used directly without extraction or purification. If desired, extraction and purification can be easily achieved using standard extraction and/or purification methods or techniques described in the literature.

The bacteria in the bacteria-based product may be in an active or inactive form. The bacteria-based products may be used without further stabilization, preservation, and storage. Advantageously, direct usage of these bacteria-based products preserves a high viability of the microorganisms, reduces the possibility of contamination from foreign agents and undesirable microorganisms, and maintains the activity of the byproducts of microbial growth.

In one embodiment, the lysate may be in a purified form or in a mixture of growth products. The lysate may be added at concentrations of 0.01 to 90% by weight (wt %), preferably 0.1 to 50 wt %, and more preferably 0.1 to 20 wt %. In another embodiment, the lysate may be in combination with an acceptable carrier, in that the lysate may be presented at concentrations of 0.001 to 50% (v/v), preferably, 0.01 to 20% (v/v), more preferably, 0.02 to 5% (v/v).

Surfactants and solvents that are useful according to the present invention include mannoprotein, beta-glucan, ethanol, lactic acid and other metabolites that have, for example, bio-emulsifying and surface/interfacial tension-reducing properties.

Upon harvesting the bacteria-based composition from the growth vessels, further components can be added as the harvested product is placed into containers and/or piped (or otherwise transported for use). The additives can be, for example, dyes, pigments, pH adjusting agents, salts, adhesion-promoting compounds, chelating agents (e.g., EDTA, sodium citrate, citric acid), solvents (e.g., isopropyl alcohol, ethanol), biocides, other microbes, and other ingredients specific for an intended use.

Advantageously, the chelating agent enhances the efficacy of the antimicrobial barrier composition by modifying the cell walls of, for example, Gram-negative bacteria, to be more susceptible to surfactant treatment. Consequently, the ability to permeate Gram-negative bacteria broadens the spectrum of antimicrobial capabilities for the subject invention.

In one embodiment, the chelating agent is selected from EDTA, citric acid, citrate, sodium acetate, or any combination thereof. The chelating agent can be added to the composition in amounts up to about 5 g/L or more. In specific embodiments, the chelating agent is EDTA at a concentration of about 0.5 to 3 g/L.

Up to, for example, 50% by weight or more of additives may be added, as needed, for particular applications, such as to vary the VOC levels, increase penetration of the mixture, decrease viscosity of the mixture, as couplers for insoluble substances in the mixture, and to provide solvents for oleophilic and hydrophilic soils.

In certain embodiments, the barrier composition of the subject invention comprises a binder, primarily responsible for holding pigments together in paints. The binder can be an oil-based binder or a latex-based binder. The binder compounds can be selected from, for example, acrylic, alkyds, acrylic acid, acrylamide, phenolic, phenolic-alkyd, polyacrylamide, polyurethanes, silicone-alkyd, polyesters, epoxies, vinyl, vinyl acetate-ethylene, vinyl-alkyd, inorganic binders (sodium, potassium ethyl silicate, lithium, etc.), organic binders (carbon-based), Tectyl® (Daubert Chemical Company, Inc., Chicago, Ill.), aliphatic-urethanes, and oil-modified urethanes.

In certain embodiments, the barrier composition of the subject invention comprises a pigment or dye, which can provide the color of paints or other coatings but can additionally protect the surface or object from UV light. Pigments or dyes can be natural, synthetic, inorganic, or organic. The pigments or dyes can be selected from, for example, titanium dioxide, zin oxide, zinc yellow, yellow dyes, benzidine yellows, chrome oxide green, phthalocyanine green, phthalocyanine blues, ultramarine blue, vermillion, pigment brown 6, red 170, dioxazine violet, carbon black, iron (II) oxide, quartz sand ($SiO_2$), talc, barite ($BaSO_4$), kaoline clay, and limestone ($CaCO_3$).

In certain embodiments, one of the solvents used in the composition is selected from mineral or organic solvents, including, for example, ethanol, butanol, propanol, aliphatic hydrocarbons, alicyclic hydrocarbons, xylene, toluene, ketones, and/or isopropyl alcohol. In a preferred embodiment, isopropyl alcohol is in an amount of 1 to 100 ml/L, more preferably from 2 to 50 ml/L, is added as to the composition.

In certain embodiments, the composition further comprises an ionic or semi-ionic liquid as a solvent. Ionic liquids can act as co-solvents and can prevent the formation of ring bonds in hydrocarbon compositions, which is one cause of hydrocarbon precipitation. Exemplary ionic liquids suitable for the subject composition include, but are not limited to, ethyl ammonium nitrate or glycerin/magnesium sulfate heptahydrate. Preferably, the concentration of the ionic liquid in the composition ranges from about 0.1% to about 5%.

Ionic liquids are composed entirely of ions, which can include cations, anions and/or a combination thereof. Many ionic liquids are in the form of organic salts with melting points below 100° C., or often even lower than room temperature. The most common ionic liquids are those prepared from organic-based cations and inorganic or organic anions. At least one ion has a delocalized charge and one component is organic, which prevents the formation of a stable crystal lattice. Ionic liquids may be suitable, for example, for use as catalysts and solvents in alkylation and polymerization reactions, as well as in dimerization, oligomerization acetylation, metatheses and copolymerization reactions. Properties of ionic liquids, such as melting point, viscosity and solubility are determined by the substituents on the organic component and by the counter-ion.

In certain embodiments, the composition further comprises ammonium hydroxide as a solvent. Preferably, the ammonium hydroxide (70% solution) is present in the composition at a concentration of about 1 to 50 ml/L, more preferably from 3 to 10 ml/L.

In one embodiment, the bacteria-based barrier product may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used, but it is preferable to use natural buffers such as organic and amino acids or their salts listed above.

In a further embodiment, pH adjusting agents include potassium hydroxide, ammonium hydroxide, Potassium carbonate or bicarbonate, hydrochloric acid, nitric acid, sulfuric acid or a mixture.

The bacteria-based barrier product may be applied with a composition that promotes adherence of the bacteria-based product to a surface to be treated. The adhesion-promoting substance may be a component of the bacteria-based product or it may be applied simultaneously or sequentially with the bacteria-based product.

Other additives typically used in coating compositions may be used, including water softening agents, sequestrants, corrosion inhibitors, and antioxidants, which are added in amounts effective to perform their intended function. These additives and amounts thereof are well within the skill of the art. Suitable water softening agents include linear phosphates, styrene-maleic acid co-polymers, and polyacrylates. Suitable sequesterants include 1,3-dimethyl-2-immidazolidinone; 1-phenyl-3-isoheptyl-1,3-propanedione; and 2 hydroxy-5-nonylacetophenoneoxime. Examples of corrosion inhibitors include 2-aminomethyl propanol, diethylethanolamine benzotraizole, and methyl benzotriazole. Antioxidants suitable for the present invention include (BHT) 2,6-di-tert-butyl-para-cresol, (BHA) 2,6-di-tert-butyl-para-anisole, Eastman inhibitor O A B M-oxalyl bis (benzylidenehydrazide), and Eastman DTBMA 2,5-di-tert-butylhydroquinone.

In certain embodiments, the composition further comprises salts and/or mineral salts selected from phosphorous, magnesium, potassium, glucose and ammonium. Preferably, from 1 to 20 g/L, and more preferably from 2 to 10 g/L of ammonium salt is added, for example, ammonium phosphate, diammonium phosphate, ammonium chloride, or another dibasic or monobasic salt.

Other suitable additives, which may be contained in the formulations according to the invention, include substances that are customarily used for such preparations. The additives can be, for example, carriers, other microbe-based compositions produced at the same or different facility, viscosity modifiers, preservatives, tracking agents, biocides, driers, plasticizers, flow control agents, defoamers, emulsifiers, UV stabilizers, anti-skinning agents, texturizers, emulsifying agents, lubricants, solubility controlling agents, preservatives, and/or stabilizers.

Advantageously, in accordance with the subject invention, the bacteria-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a bacteria-based composition can typically be stored at ambient temperatures.

The compositions according to the subject invention can comprise ingredients in amounts effective to clean the surfaces, formations, and equipment, and/or to provide an effective coating to prevent future buildup of contaminants, scale and corrosion.

Use of Microbes and their Biofilm Lysates in Barriers

The use of bacterial-derived barriers can provide a variety of improvements upon application to an object and/or surface.

Enhanced Performance and Longevity of a Barrier

In certain embodiments, the application to an object of the subject compositions or methods enhance the performance of a barrier, primarily through the modification of the interaction between the object and its surrounding. In certain embodiments, the bacteria and/or the lysate and/or molecules (such as proteins) obtained from the bacterial biofilm may be applied to a surface of an object, which may prevent or limit direct contact by living organisms or non-living substances, prevent fouling by living organisms or non-living substances, sequester living organisms or non-living substances, inactivate living organisms or non-living substances, enhance barrier durability, and/or increase the concentration of commensal organisms. In some embodiments, the molecules have been synthetically produced and/or purified.

In certain embodiments, the subject invention provides a self-decontaminating surface.

In certain embodiments, the composition can prevent a direct contact of a contaminant by a physical separation of the environment in which the object or surface resides from the object itself. Paints, varnishes, lacquers, polishes, mucous and other barriers provide a physical separation between the environment and object within the barrier.

In certain embodiments, the composition can prevent fouling by living organisms, such as viruses and bacterial cells. The composition can prevent colonization of a surface and prevent biofilm adhesion, which can limit the spread of disease-causing bacteria. The composition can also stop the growth of organisms or initiate cell apoptosis.

In certain embodiments, the composition of the subject invention can prevent fouling by inanimate substances such as salt deposits.

In certain embodiments, the composition of the subject invention can enhance the durability of a barrier. This can be accomplished by resisting frictional abrasion from liquids, gases, or solids.

In certain embodiments, the composition of the subject invention can increase the concentration of commensal organisms on the object or surface. This can be done indirectly, by inhibiting the growth or adhesion of microbial competitors to the commensal organism on the surface. Or, the composition can directly enhance the growth rate of the commensal organism.

The subject invention can be used for preventing deposition from occurring. Dispersal, or dissolution, of organisms or precipitates decreases the concentration of contaminants available on the surface or object. Thus, the present invention allows for delaying or completely removing the necessity for preventative maintenance related to removing precipitates and deposits, as well as the need for replacing or repairing equipment parts. The subject coating composition can further be applied for the dispersal of scale buildup in, for example, storage and transportation tanks, tankers, ships, trucks, pipelines and flowlines, concrete, asphalt, mulch, metals, siding, and stucco without need for mechanical cleaning solutions or toxic solvents.

In certain embodiments, the methods are used to clean a surface, wherein the surface is equipment in need of decontamination, defouling, and/or unclogging. Advantageously, the methods of the subject invention can be used to improve overall productivity of an industrial operation or a piece of equipment by improving the maintenance and proper functioning of equipment.

Applying the Composition to Surface

The composition can be applied to inanimate or animate surfaces or objects, such as skin, mucous membranes, clothing, metal surfaces, eyewear, protective wear (including masks), and footwear.

In certain embodiments, the subject invention provides a self-decontaminating surface.

In certain embodiments, the composition can be applied to bandages; personal hygiene products; dishes and utensils; tables and countertops; clothing, including vests, shirts, pants, socks, jackets, skirts, shorts, underwear, hosiery, gloves, scarves, armor, diving suits, swimsuits, space suits, formalwear, activewear, leatherwear, leisurewear; footwear including shoes, boots, sandals, slippers, swimfins, cleats, boat shoes, clogs, cleats, snowshoes, ski boots, sailing boots, pointe shoes, high-heeled footwear; headwear including hats, helmets, crowns, caps, bonnets, hoods, masks, turbans, veils, wraps, wigs, or medical device; eyewear including glasses, goggles, contact lenses, blindfolds, eye shields, and sunglasses; clothing accessories including bracelets, rings, bags, satchels, packs, purses, necklaces, jewelry, watches, umbrellas, wallets, parasols, hand fans, swords, canes, ties, sashes, shawls, lanyards, pins, piercings, and stockings.

In certain embodiments, the composition can be applied to a vehicle including military vehicles, armored fighting vehicles, reconnaissance vehicles, self-propelled anti-aircraft guns, self-propelled air defense system, ambulances, cars, trucks, jeeps, Humvees, vans, helicopters, bicycles, unicycles, scooter, skateboards, wagon, bus, hovercraft, and motorcycles; boats or warships including, submarines, trawlers, drifters, patrol vessels, destroyers, aircraft carriers, frigates, corvettes, battleships, battlecruisers, gunboats, and minehunters; trains including armored trains, passenger trains, freight trains, locomotives, maglev, monorail, and mine trains; airplanes including jet, propeller, or rocket propelled varieties; spacecraft including satellites, probes, rockets, pods, capsules, and orbiters.

The composition can be applied to the surface by spraying using, for example, a spray bottle or a pressurized spraying device. The composition can also be applied using a cloth or a brush, wherein the composition is rubbed, spread or brushed onto the surface. Furthermore, the composition can be applied to the surface by dipping, dunking or submerging the surface into a container having the composition therein.

In one embodiment, the material and/or surface is allowed to soak with the composition thereon for a sufficient time to apply the coating or lift and/or remove the contaminant from the object and/or surface. For example, soaking can occur for 12 to 24 to 36 to 48 to 72 hours or more, as needed.

In one embodiment, the method further comprises the step of removing the composition and contaminant from the surface. This can be achieved by, for example, rinsing or spraying water onto the surface, and/or rubbing or wiping the surface with a cloth until the composition and contaminant have been freed from the surface. Rinsing or spraying with water can be performed before and/or after rubbing or wiping the surface with a cloth.

In another embodiment, mechanical methods can be used to remove the contaminant and/or composition from the surface. For example, an agitator, drill, hammer, or scraper can be used for freeing contaminants from surfaces that are particularly difficult to remove due to, for example, the amount of contaminant or the type of contaminant.

In certain embodiments, the composition can be applied in a pharmaceutically-acceptable manner including, injection (i.e., subcutaneous, intravenous, intraperitoneally), orally, dermally or intranasally.

Materials and Methods
Bacterial Strains and Culture Media

*Lactobacillus fermentum* Qi6 (Lf Qi6) was grown in MRS media at 37° C.

Methicillin-resistant *Staphylococcus aureus* (MRSA) ATCC 33591 (ATCC, Manassas, Va.) was stored in tryptone soya broth (TSB) (Thermo Scientific, Waltham, Mass.) containing 20% (v/v) glycerol at −80° C. The culture was incubated overnight at 37° C., aerobic, on a rotary shaker at 110 rpm. The optical density of the overnight culture was read with spectrophotometer (SpectraMax Plus384, Molecular Devices, Sunnyvale, Calif.) and diluted to $OD_{600}$ of 0.2. The strain was also subjected to both met and eap PCR using established protocols to confirm MRSA status (3).

Culture of Lf Qi6 Biofilm

Lf Qi6 was cultured in MRS agar plate. The culture was then incubated in 5 ml of MRS broth for 24 h at 37° C. 1 ml of the culture was transferred into a T-150 tissue culture plate with 25 ml of MRS broth. 25 ml of MRS media was changed every 48 hours to allow the biofilm of Lf Qi6 to grow as lawn on the bottom of the culture plate. The culture was then grown for 7 days to produce a thick biofilm layer. The grown biofilm layer was subsequently scraped out and suspended in fresh medium. Freezer stacks were made with glycerol and stored in −80° C.

A biofilm phenotype of Lf Qi6 in frozen stock was cultured in 10 ml of fresh MRS media for 24 hour at 37° C. 10 ml of culture was inoculated into 25 L of MRS media with 500 g sterile glass wool. The biofilm was then cultured for 72 h under static conditions at 37° C. The culture was mixed every 24 h with a gentle shaking, after which the media and glass wool were harvested. The biofilm cells were subsequently detached from the glass wool via sonication. The cells were further centrifuged to concentrate the biofilm of Lf Qi6, which was then suspended in sterile water. This scale-up yields a biofilm culture at a concentration of 2 g/L.

Lf Qi6 Biofilm Downstream Processing 50 g of the Lf Qi6 biofilm was suspended in 1 L of sterile water. The suspension was gently mixed for 24 hours at room temperature to allow the passive release of multiple bioactives. The mixture was then sonicated for 30 minutes (50 KHz, 200 watt) into uniform lysate using an OmniSonic Ruptor 400. The sonicated lysate was then frozen and lyophilized into a fine powder.

Preparation of if Qi6 from Probiotic Bacteria

*L. fermentum* Qi6 was grown in MRS media using proprietary culture methods. Bacteria were then subcultured into 500 ml MRS medium for an additional period, again using proprietary culture methods. Bacteria were sonicated (Reliance Sonic 550, STEMS Corporation, Mentor, Ohio, USA), centrifuged at 10,000×g, cell pellets dispersed in sterile water, harvested cells lysed (Sonic Ruptor 400, OMNI International, Kennesaw, Ga., USA) and centrifuged again at 10,000×g, and soluble fraction centrifuged (50 kDa Amicon Ultra membrane filter, EMD Millipore Corporation, Darmstadt, Germany, Cat #UFC905008). The resulting fraction was distributed into 0.5 ml aliquots, flash frozen in liquid nitrogen and stored at −80° C.

Biofilm Inhibition Assay

MRSA was added to the wells of sterile polystyrene, tissue-culture (TC) treated, flat-bottom plates (Genesee Scientific, San Diego, Calif., Cat #25-109). TSB served as sterility control. Growth control wells received equal parts MRSA and culture medium. Chosen concentrations of Qi601S or other test agents were added, the plate incubated at 37° C. for 18 h and then biofilm was quantified as described in the staining and biofilm quantification section.

Staining and Biofilm Quantification

The tissue culture plate was washed three times with PBS using the BioTek plate washer and placed in a 47° C. incubator for one hour to heat-fix the biofilm. The plate was cooled to room temperature, stained with 0.1% (v/v) crystal violet for 15 min, then washed with deionized $H_2O$ using the microplate washer. 100% ethanol was added for 30 min in order to dissolve crystal violet stain. The plate was read at 590 nm and 600 nm using a spectrophotometer (SpectraMax Plus 384, Molecular Devices, Sunnyvale, Calif.).

EXAMPLES

A greater understanding of the present invention and of its many advantages may be had from the following examples, given by way of illustration. The following examples are illustrative of some of the methods, applications, embodiments, and variants of the present invention. They are not to be considered as limiting the invention. Numerous changes and modifications can be made with respect to the invention.

Example 1—Qi601SL, Qi601SML, Qi601A, Qi601AM, and Qi601SP Inhibit Adhesion of MRSA (FIG. 2, FIG. 6, FIG. 7, FIG. 8)

To demonstrate that the various versions of the lysates from *Lactobacillus fermentum* Qi6 can inhibit adhesion of MRSA, MRSA is first grown to log phase, diluted with TSB and then various varieties of Qi601S (Qi601SL, Qi601SML, Qi601SP, Qi601AM, or Qi601A) are added to the MRSA in a 96-well or 24-well plate. The cultures are incubated overnight. Each of the samples is visualized for adhesion using crystal violet staining and a plate reader measuring light absorbance at 590 nm.

that Lf Qi601 lysates can inhibit adhesion of MRSA, establishing a novel method to inhibit MRSA biofilm adhesion.

Example 2—Qi601SL, Qi601SP, Qi601SML, Qi601A, Qi601AM, and Qi601SMP Continue to Inhibit Adhesion of MRSA after Washing (FIG. 1, FIG. 3, FIG. 4, FIG. 5, FIG. 7, FIG. 8)

To demonstrate that the various versions of the lysates from *Lactobacillus fermentum* Qi6 can inhibit adhesion of MRSA, MRSA is first grown to log phase, diluted with TSB and then various varieties of Qi601S (Qi601SL, Qi601SML, Qi601SMP, Qi601SP, Qi601A, or Qi601AM) are added to the MRSA in a 96-well or 24-well plate. The cultures are incubated overnight. Each of the samples is visualized for adhesion using crystal violet staining and a plate reader measuring light absorbance at 590 nm.

While it is significant, that the lysates can inhibit MRSA adhesion as demonstrated in both Example 1 an Example 2, the ability of the lysate to maintain its effects after washing, demonstrating durability of the composition.

Example 3—Atomic Force Microscopy

FIG. 9 provides an atomic force microscopy image of the material of the subject invention.

Example 4—Prevention of Pathogen Attachment

Pathogen attachment to human tissues is indispensible to its pathogenicity, particularly for the food poisoning strain, *E. coli* O157:H7. Therefore, the anti-adhesive effect of Qi 601S on human intestinal cells for the model gram negative pathogen *E. coli* was evaluated. These results (FIG. 10) in human cells demonstrate that treatment with Qi601S creates an *E. coli*-resistant anti-adhesive surface.

FIG. 10 shows how Qi 601S creates an anti-adhesive surface on Caco-2 cells effective against *E. coli*. Cells were split into 24 well plates at $5 \times 10^4$ cells per well and grown for an additional 10 days for differentiation and confluency. Selected wells received overnight pre-treatment with Qi 601S 0.1% v/v followed by PBS wash. *E. coli* K12 was expanded overnight in TSB, $1 \times 10^8$ CFU added to each well and incubated for 3 h. Unbound bacteria were removed by PBS wash. Intestinal cells were lysed with 1% Triton X-100. Bound bacteria were quantified by serial dilution and standard plate counts on TSA and compared against untreated control.

Durability of the anti-microbial anti-adhesive (self-cleaning) activity of Qi 601S at 48 hours was also demonstrated on living human tissue. Human ex vivo full thickness skin specimens (excess tissue from elective abdominoplasty procedures obtained immediately after removal) were used to represent in vivo protection.

Briefly, the method was as follows: ex vivo skin was pre-qualified as MRSA-negative by standard culture method. Colonies were identified phenotypically on MRSA-selective media (CHROMagar, Becton Dickinson) per package instructions. Abdominoplasty skin was maintained in continuous culture, used within 2 weeks of surgical excision after 3 days of media changes to remove residual pre-operative antibiotics. One centimeter punch biopsies were obtained from single-donor explant tissue, and experiments performed in replicates of 5 in 24-well plates.

Epidermis was with vehicle (300 ul PBS) or Qi601S (1% in 300 ul PBS) for 24 hours. Skin was then rinsed with PBS×3 and placed in 0.5 micron transwell inserts of new culture plates. Experimental samples were then incubated with 5 ul MRSA at OD=0.1 ($1 \times 10^9$ CFU/ml)×48 hours, rinsed again with PBS to remove non-adherent bacteria and transferred to petri dishes. Each skin sample was swabbed 3 times, and swab tips placed collectively into a tube containing 0.1% Triton-X in PBS with glass beads and then vortexed×15 seconds. Serial dilutions were plated on Luria Bertani (LB) agar and CHROMagar and colonies counted the next day.

FIG. 11 shows the anti-adhesive surface against MRSA produced by Qi 601S. Qi 601S at 1% v/v in PBS was applied to living human skin in culture for 24 hours and then rinsed. Skin was then incubated with MRSA for 2 days, skin rinsed and then cultured for MRSA colonies. Pre-treatment with Qi 601S demonstrated an over 60% significant reduction in MRSA load compared with untreated skin.

Example 5—Protection Against Biological Threats

In addition to activity against MRSA biofilms, Qi 601S has demonstrated activity against other biological threat agents, including viral threats. Biological Warfare Agents have been classified by the CDC, into 3 categories based on biodefense, biological warfare and bioterrorism risk. Category A includes readily disseminated or transmitted biological agents such as anthrax, Category B includes moderately easy to disseminate or transmit biological agents such as *Salmonella, E. coli* O157:H7 and *S. aureus*, particularly MRSA, and Category C includes emerging agents. Category C is under continual re-evaluation. For instance, coronavirus was added in 2014 by NIAID, CDC and United States Department of Homeland Security to Category C, which now includes Severe Acute Respiratory Syndrome-associated Coronavirus (SARS-CoV), MERS-CoV, and other highly pathogenic human coronaviruses, including COVID-19 (NIAID Emerging Infectious Diseases/Pathogens, 2018).

Qi 601S has also demonstrated complete protection against acetylcholinesterase (AChE) inhibition. This enzyme is critical for normal nerve response and function and its inhibition is the target of nerve gas agents, which are irreversible AChE inibitors. Irreversible inhibition of this enzyme leads to over-excitation of the nervous system and eventual death. AChE degrades the excitatory neurotransmitter acetylcholine (Ach) into choline and acetic acid at the neuronal synapse and is mainly found at the cholinergic synapses in the central nervous system.

Lethal at microgram amounts, organophosphates (OP) have been used as insecticides and nerve gas agents. Although these chemicals are among the most toxic compounds known, there are currently no non-destructive methods for the decontamination of exposed victims.

Potential AChE activity protection of Qi601S was tested against the enzyme inhibitory activity of donepezil using a standard assay kit (Abcam, #138871). Results, FIG. 13, indicate a strong, complete and consistent level of AChE protection with 2% Qi601S when challenged with increasing doses of donepezil hydrochloride.

Example 6—Activity and Stability

The safety profile of the compositions of the subject invention enable biomedical application as a self-decontaminating material applied topically to the skin, nose, eye and inhaled into the lungs. A single application of 1% solution of the heat stable, hydrophilic fraction Qi 601S provides non-toxic anti-coronavirus protection in an in vitro SARS CoV model for 5+ days and durable anti-MRSA anti-adhesion on human skin for up to 2 days (latest time point tested) as well as inert hydrophobic surfaces (polypropylene and glass) despite repeat rinsing and over an at at least 4.5 to 7.5 pH range. Unlike many biological products, this fraction remains stable when subjected to temperatures greater than 121° C., repeat freeze-thaw, and in aqueous vehicle. Maintenance of anti-MRSA effect when tested as an ammonium sulfate precipitate and compositional analysis of chemically purified biosurfactant indicate that antimicrobial and surfactant activities are protein-derived.

that, when the composition is applied to a surface, that surface becomes less susceptible to microbial contamination; and wherein said *Lactobacillus* spp. is *L. fermentum* Qi6 having Accession No. PTA-122195.

2. The method of claim 1, wherein the surface is selected from skin, intestine, stomach, lung, eye, mouth, nose, ear, trachea, vagina, or esophagus of a subject.

3. The method of claim 1, wherein the surface is selected from medical instruments, countertops, protective suits, tables, appliances, chairs, dishes, utensils, medical implants, personal hygiene products, bandages, clothing, eyewear, footwear, headwear and masks.

4. The method, according to claim 1, wherein the surface is on an object selected from vehicles, boats, ships, cars, trucks, tanks, airplanes, and trains.

5. The method of claim 1, wherein performance and/or longevity of the surface of an object is enhanced by preventing or limiting direct contact with the surface by a living organism.

6. The method of claim 1, wherein the surface is of a vagina.

7. A method for enhancing a barrier against microbial contamination of a surface, wherein said method comprises

What is claimed:

1. A method for enhancing a barrier against microbial contamination of a surface, wherein said method comprises applying to the surface a composition comprising inactivated *Lactobacillus* spp. that had been grown as biofilm, wherein the composition enhances a barrier function such applying to the surface a composition comprising inactivated *Lactobacillus* spp. grown as biofilm wherein, when the composition is applied to a surface, that surface becomes less susceptible to microbial contamination; and wherein the inactivated *Lactobacillus* is *L. fermentum* Qi6 having Accession No. PTA-122195, and wherein the surface is selected from protective suits, medical implants, personal hygiene products, bandages, clothing, eyewear, footwear, and masks.

8. A method for providing a barrier against microbial contamination of a surface, wherein said method comprises applying to the surface a composition comprising an isolated protein comprising SEQ ID NO: 1.

9. The method of claim 8, wherein the surface is selected from skin, intestine, stomach, lung, eye, mouth, nose, ear, trachea, vagina, or esophagus of a subject.

10. The method of claim 8, wherein the surface is selected from medical instruments, countertops, protective suits, tables, appliances, chairs, dishes, utensils, medical implants, personal hygiene products, bandages, clothing, eyewear, footwear, headwear, and masks.

11. The method of claim 8, wherein the surface is on an object selected from vehicles, boats, ships, cars, trucks, tanks, airplanes, and trains.

\* \* \* \* \*

SEQUENCE LISTING

```
<160> NUMBER OF SEQ ID NOS: 2

<210> SEQ ID NO 1
<211> LENGTH: 74
<212> TYPE: PRT
<213> ORGANISM: Lactobacillus fermentum

<400> SEQUENCE: 1

Met Asp Asn Arg Ile Phe Phe Asn Pro Gly Asp Ser Ile Ala Asn Ile
1               5                   10                  15

His Asp Tyr Asn Glu Ala Val Arg Lys Gly Gln Ile Phe Lys Lys Glu
            20                  25                  30

Gln Gln Ala Gly Asp Leu Val Ile Ala Lys Gly Pro Asp Asp Glu Glu
        35                  40                  45

Tyr Ala Ile Phe Tyr Ala Asn Asp Ala Leu Pro Ala Asp His Glu Gln
    50                  55                  60

Ser Gln Pro Tyr Glu Ile Lys Lys Asn Leu
65                  70

<210> SEQ ID NO 2
<211> LENGTH: 225
<212> TYPE: DNA
<213> ORGANISM: Lactobacillus fermentum

<400> SEQUENCE: 2
atggataacc ggattttctt caaccccggc gactcgatcg ccaacatcca cgactacaac      60
gaagccgtcc gcaagggcca aatcttcaaa aaggaacagc aggccggcga cctcgtgatc     120
gctaagggtc ccgatgacga agaatacgcc atcttctacg ccaacgatgc cctgcccgcc     180
gaccacgagc aatcccaacc ctacgagatt aagaaaaacc tctaa                    225
```